United States Patent
Adachi et al.

[11] Patent Number: 6,074,568
[45] Date of Patent: Jun. 13, 2000

[54] DRY ETCHING METHOD

[75] Inventors: Kouichiro Adachi; Satoshi Morishita; Kazuo Sugimoto, all of Tenri, Japan

[73] Assignee: Sharp Kabushiki Kaisha, Osaka, Japan

[21] Appl. No.: 09/002,707

[22] Filed: Jan. 5, 1998

Related U.S. Application Data

[62] Division of application No. 08/637,349, Apr. 24, 1996, Pat. No. 5,733,820.

[30] Foreign Application Priority Data

| Apr. 27, 1995 | [JP] | Japan | 7-103649 |
| Jun. 29, 1995 | [JP] | Japan | 7-163989 |
| Dec. 28, 1995 | [JP] | Japan | 7-343067 |

[51] Int. Cl.$^7$ .................................................. G01L 21/30
[52] U.S. Cl. ........................... 216/59; 216/60; 438/14; 438/7
[58] Field of Search ........................ 438/7, 8, 9, 14; 216/59, 60, 61; 118/712, 713

[56] References Cited

U.S. PATENT DOCUMENTS

| 4,430,151 | 2/1984  | Tsukada .         |         |
|-----------|---------|-------------------|---------|
| 4,472,237 | 9/1984  | Deslauners et al. |         |
| 5,169,407 | 12/1992 | Mase et al.       | 29/25.01|
| 5,234,526 | 8/1993  | Chen et al.       |         |
| 5,245,157 | 9/1993  | Ohiwa .           |         |
| 5,320,704 | 6/1994  | Horioka et al.    |         |
| 5,374,322 | 12/1994 | Imahashi et al.   |         |
| 5,536,359 | 7/1996  | Kawada et al.     | 156/626.1 |
| 5,863,807 | 1/1999  | Jang et al.       | 438/14  |
| 5,877,032 | 3/1999  | Guinn et al.      | 438/9   |

FOREIGN PATENT DOCUMENTS

| 4-334021 | 11/1992 | Japan . |
| 5-304118 | 11/1993 | Japan . |
| 6-188221 | 7/1994  | Japan . |
| 7-75230  | 8/1995  | Japan . |

*Primary Examiner*—Bruce Breneman
*Assistant Examiner*—Luz Alejandro
*Attorney, Agent, or Firm*—Nixon & Vanderhye P.C.

[57] ABSTRACT

A method for diagnosing a function of plasma etching apparatuses and a method for estimating selectivity in an actual etching process in fabrication of semiconductor devices involves generating plasma of a gas mixture including halogen and oxygen in a predetermined condition. An intensity of one of first emissions from the plasma at a first wavelength and an intensity of one of second emissions from the plasma at a second wavelength is measured A ratio of the intensity of the one of first emissions to that of the one of second emissions is obtained. The obtained emission intensity ratio is compared with an emission intensity ratio which is previously measured for a plasma condition when the plasma etching apparatus operates normally.

6 Claims, 21 Drawing Sheets

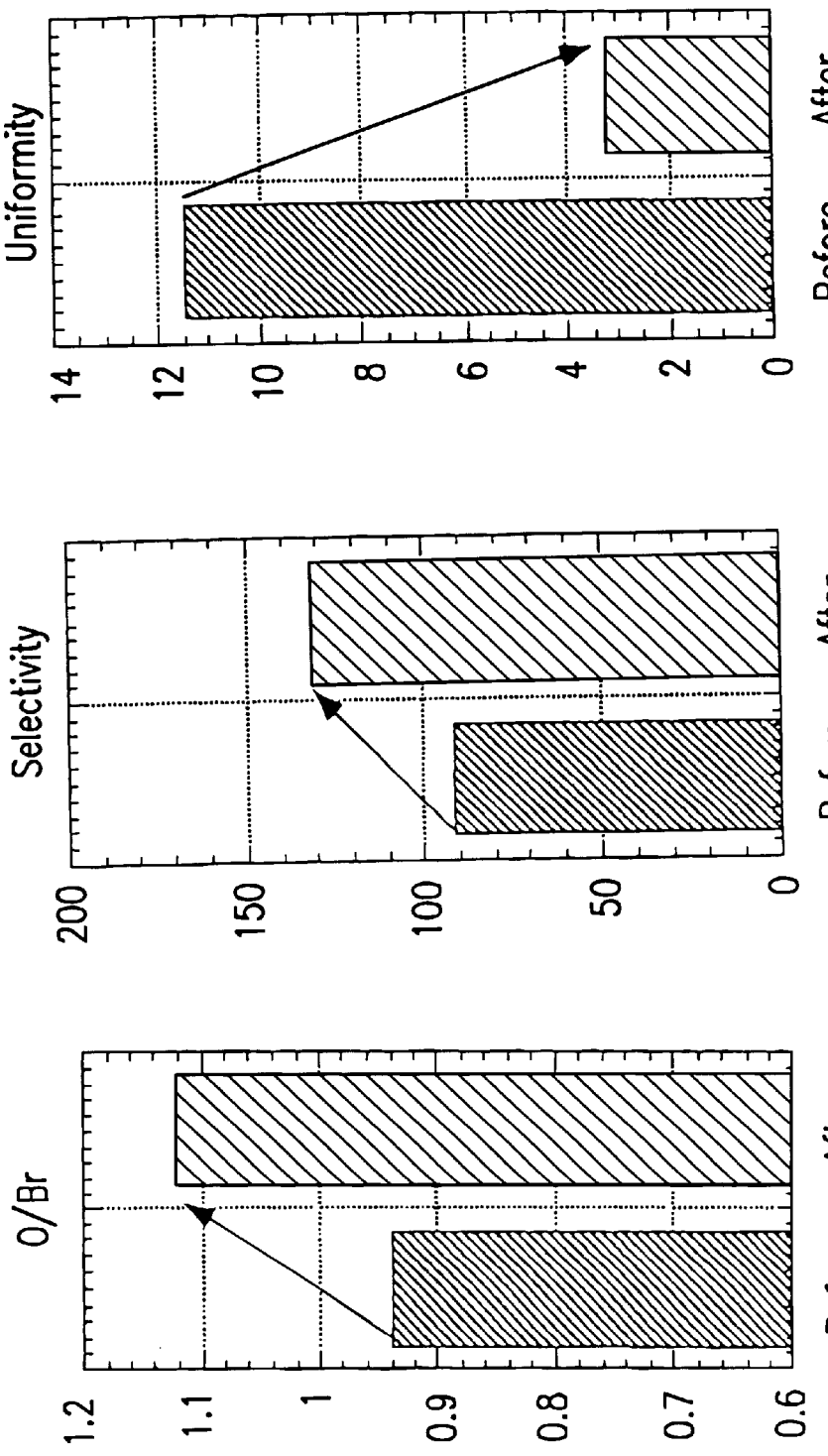

FIG. 13
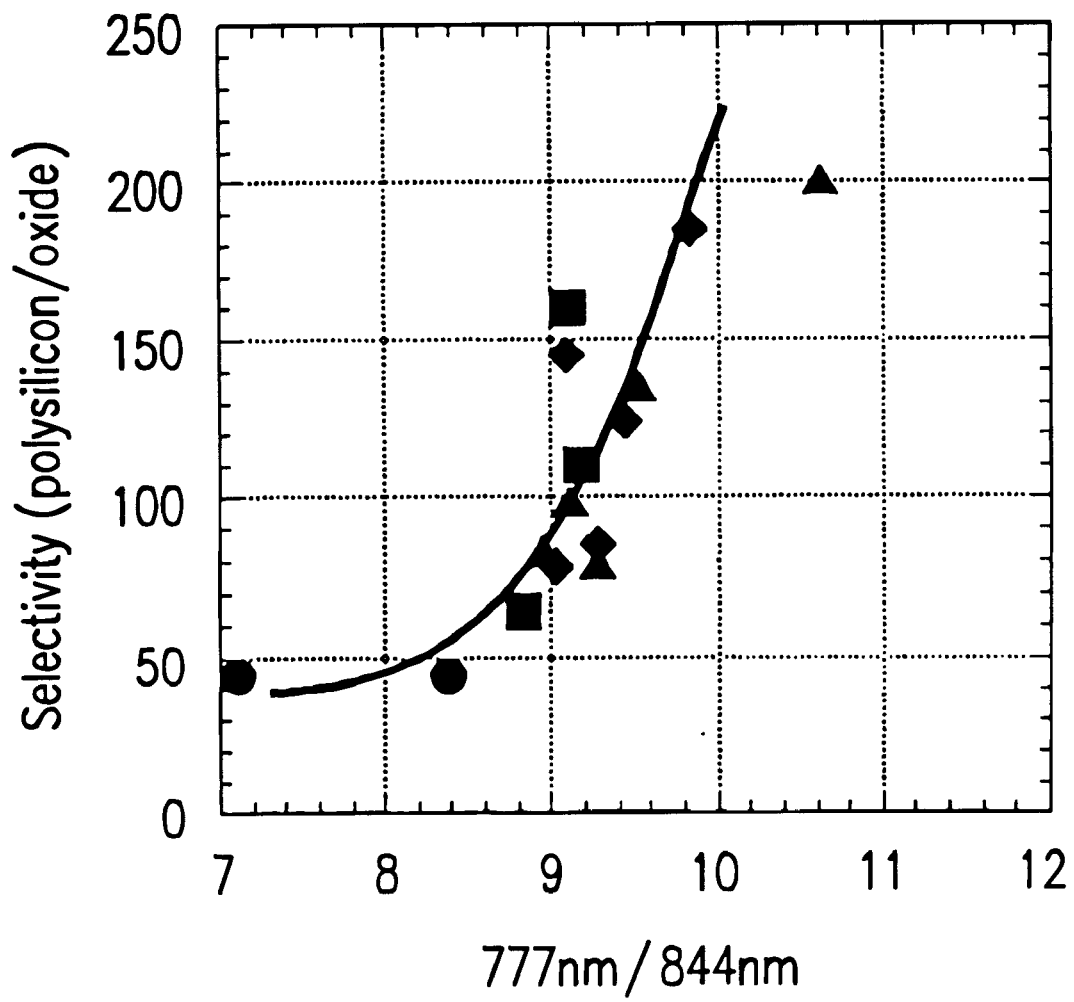
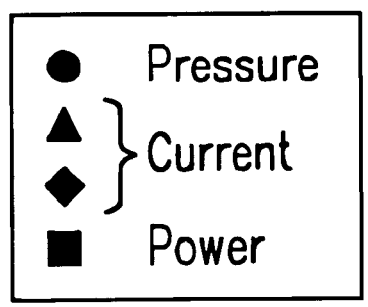

FIG. 14
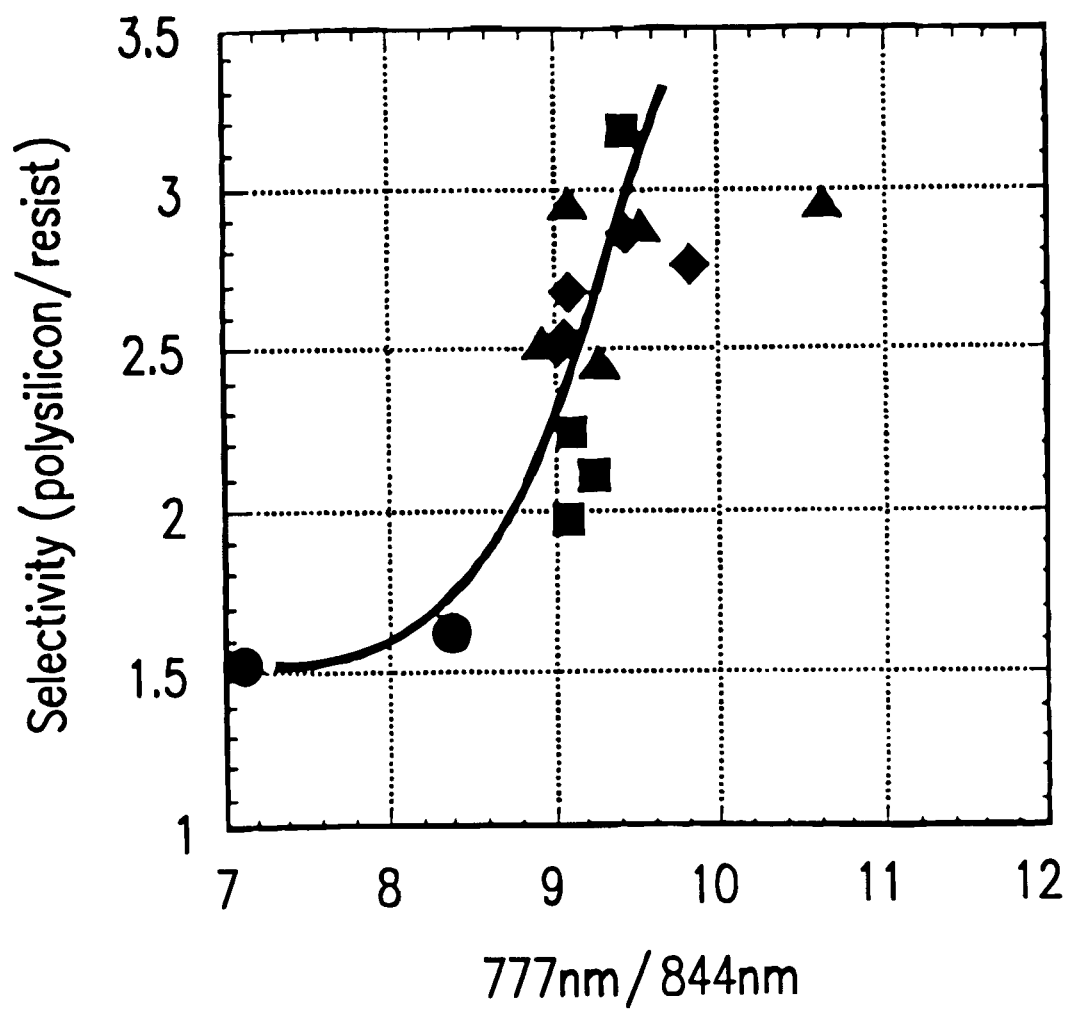
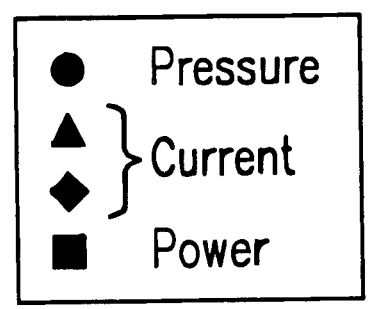

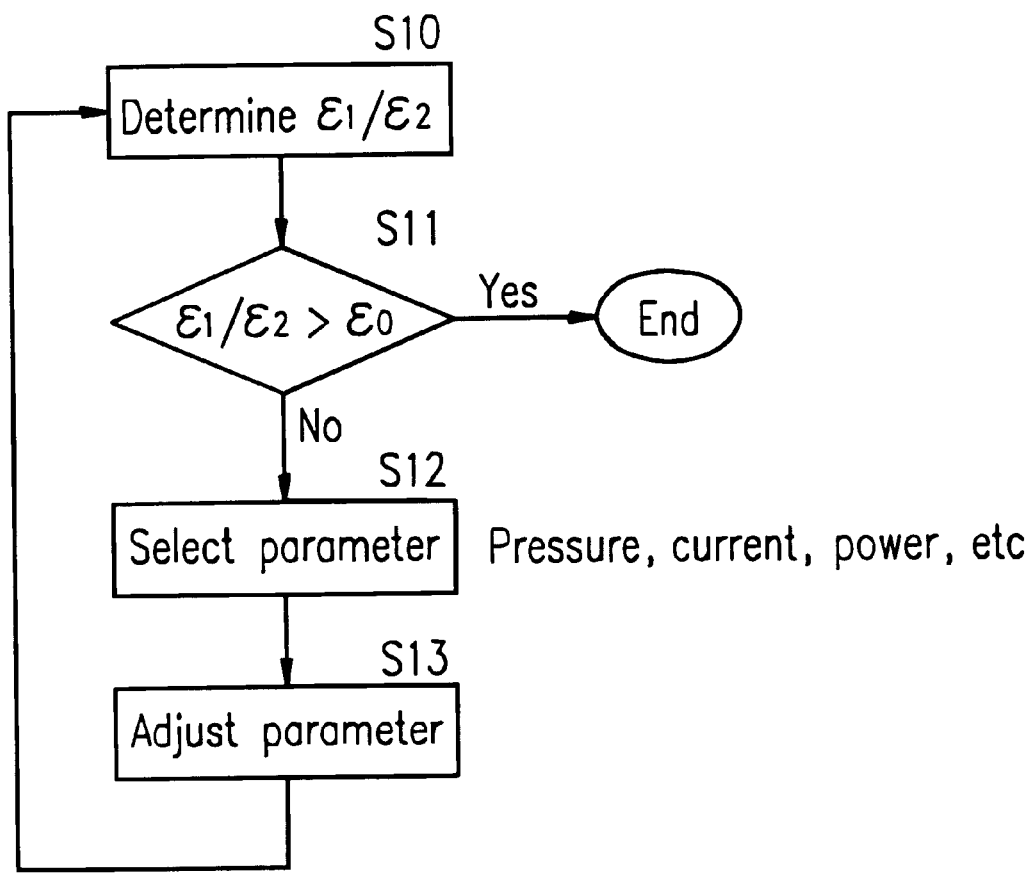

DRY ETCHING METHOD

This is a division of application Ser. No. 08/637,349, filed Apr. 24, 1996, now U.S. Pat. No. 5,733,820.

BACKGROUND OF THE INVENTION

1. Field of the Invention

The present invention relates to a method of dry etching, and more particularly, to a method of plasma etching used for manufacturing semiconductor devices.

2. Description of the Related Art

Recently, as semiconductor devices have become more highly integrated, higher performance in size precision of the patterning processes has been required in order to keep up with progress in the microminiaturization of electronic circuits. Consequently, etching of silicon material (e.g., silicon and material including silicon), typically used for gate electrodes of MOS transistors, has gradually shifted from isotropic wet etching to anisotropic dry etching. For example, reactive ion etching (RIE), electron cyclotron resonance (ECR) plasma etching, and the like are used. In such plasma etching processes, thin layers of silicon material or substrates are patterned by removing particles (atoms, molecules) from a solid surface of the material, using chemical and physical reactions between the solid surface and radicals and ions which are generated in the plasma.

Halogen/halide gas etchant such as fluorine-based etchants, Freon (chlorofluorocarbon)-based etchants, and the like have been used conventionally for silicon material plasma etching. Recently, chlorine-based etchants such as $Cl_2$ and bromine-based etchants such as HBr have been used because the chlorine-based and bromine-based etchants produce anisotropic images which fluorine-based and Freon-based etchants do not. The volatility of reaction products produced by etching reactions between the chlorine-based and bromine-based etchants and silicon material is relatively low so that the etching process does not progress automatically, (i.e., the etching process is progressed-by an ion-assist mechanism). In addition, bond energies $E_{bond}$ of chlorine and bromine to silicon are lower than those of fluorine and Freon to silicon, (i.e., $E_{si-F} > E_{si-O} > E_{si-Cl} > E_{si-Br}$). Thus, chlorine-based and bromine-based etchants increase the etching selectivity of silicon material layers to oxide underlayers compared with fluorine-based and Freon-based etchants.

As semiconductor devices become more highly integrated, the thickness of oxide underlayers (for example, gate insulating films made of a material such as silicon oxide under silicon material gate electrodes) also has been reduced. Accordingly, in patterning silicon material, it is important to improve the selectivity between the silicon material layers and the silicon oxide layers minimize damage to the silicon oxide layers, and improve the size precision. A new dry etching technique is required which satisfies these requirements of high selectivity, less damage, and high size precision.

(1) Conventional ECR Plasma Etching Apparatus

FIG. 1 shows an example of ECR plasma etching apparatus 200 which utilizes microwaves. As shown in FIG. 1, in the plasma etching apparatus 200, a magnetron 201 generates the microwaves of 2.45 GHz, a waveguide 202 introduces the microwaves into a vacuum chamber 204 through a window 203. Solenoid coils 205 generate a magnetic field 206 in the vacuum chamber 204. The plasma 207 is generated by cyclotron motion of electrons caused by the multiplier effect of the magnetic field 206 and the electric field of the microwaves.

The solenoid coils 205 are usually divided into at least two coils in order to increase uniformity of the plasma and controllability for the plasma. By varying independently electric current values of the respective coils so an to change position of en ECR region and gradient of the magnetic field 206, the efficiency of the microwave power and the density distribution of the plasma 207 can be changed. The ECR region is a region satisfying an ECR condition of magnetic field strength of 875 Gauss in the magnetic field 206. The electric current values of the solenoid coils 205 are detected by a power meter 208.

A directional coupler 209 detects incident and reflected microwaves traveling through the waveguide 202. Power (intensity) of the incident and reflected waves is indicated by power meters 210 and 211, respectively. A signal 221 which represents the power of the reflected wave is sent to a control circuit 212 from the power meter 211. The control Circuit 212 adjusts the microwaves and minimizes the signal 221 by Changing positions of stub pins 213 which are driven by motors, so as to minimize the reflected energy and maximize an incident power of the microwaves.

As shown in FIG. 1, a wafer 214 to be etched is placed on a wafer platen electrode 216 in a reaction chamber 215. The wafer platen electrode 216 is connected to a high frequency power supply 217 and is supplied with a high frequency bias voltage. Process gas is introduced from a gas inlet 218 into the vacuum chamber 204, is used for etching, and then is exhausted through a gas exhaust 219.

In order to improve the size precision of plasma etching as described above, it is important to obtain a plasma condition suitable for fabrication of semiconductor devices by optimizing process parameters such as gas pressure and gas flow rate. More specifically, it is important to measure and obtain a preferable value of selectivity (the ratio of etch rates) in the plasma. For example, it is required to perform an end point detection (EPD) effectively and precisely in order to measure the selectivity. An example of EPD is described in Japanese Patent Publication No. 7-75230, in which density ratios of ions and radicals are monitored by using a mass analyzer.

(2) Selectivity

Selectivity is conventionally obtained by measuring actual etch rates. For example, changes in thickness of layers before and after the etching process of sample wafers are measured using an optical measuring device so as to calculate the selectivity from the measurement results. Scanning electron microscopes (SEM) are also used to observe cross-sections of the sample wafers to determine the selectivity.

However, it is time and labor consuming to measure etch rates for various process conditions by using many sample wafers. Thus, empirical knowledge such as experimental data for other etching apparatuses and available information from academic journals and the like are utilized in order to estimate etch rates. For example, a shortage in the number of actual measurements is compensated by making predictions using empirical laws such that a lower discharge voltage in the vacuum chamber is preferable. However, when the process parameters are peculiar for one etching apparatus, it is difficult to make a prediction for another etching apparatus based on the process parameters. In addition, as the number of the process parameters used for controlling the plasma condition is increases, it becomes difficult to make a comprehensive decision for setting the process parameters.

For example, in the case where a certain condition which provides an optimum value of one process parameter is found to be a particular one, the optimum value of the process parameter should be measured again by varying the process parameter under other conditions so as to re-set a general optimum value.

As a more specific example, obtaining optimum values of process parameters (RF power and gas pressure) for improving etch rate is described below. With initial conditions of RF power 100 W and pressure 0.5 Pa, and by varying the RF power while maintaining pressure of 0.5 Pa, it is assumed that an optimum value 80 W of the RF power is obtained for the highest etch rate. After similar measurements for other pressure values, it is revealed that the pressure value of 0.5 Pa is a particular condition and the optimum value of the RF power for other pressure values is 120 W. In such a case, the first measurement for the pressure value of 0.5 Pa would be useless.

Furthermore, in the case where the selectivity is dependent upon a plurality of process parameters, for example, both pressure and RF power, in order to find which of pressure and RF power parameters the selectivity most strongly depends on, it is necessary to perform a large number of measurements using many sample wafers. Determining the dependency of the selectivity on a plurality of process parameters requires a large number of measurements that usually cannot be performed effectively.

In addition, in the case where the process parameters cannot be varied separately due to intrinsic characteristics of the etching device, it is difficult to determine an optimum value for each of the process parameters. For example, total gas flow and gas pressure are not independent, and an increase of the total gas flow increases the pressure and vice versa.

As described above, the conventional methods of measuring the selectivity and determining optimum values of the process parameters for obtaining high selectivity have many problems to be solved.

(3) Size Precision of Etching Process

Size precision of plasma etching is determined by profile variations in resist masks and those in films or substrates which are subjected to etching during the etching process. Therefore, these variations in the etching process (referenced as process etch biases) should be reduced in order to improve size precision.

Plasma etching of silicon material is usually performed using organic resist masks which are used as etching masks in photolithography processes, and using halide gas plasma au an etchant. Using organic resist masks reduces the number of fabrication steps for forming the etching masks which are required for silicon oxide masks. Thus, organic resist masks are advantageous for improving the size precision and reducing the cost by reducing the number of fabrication steps. In addition, etching residues are likely to occur in stop portions of patterns when silicon oxide films are etched to form resist masks. Etching residues are not likely to occur in forming organic resist masks. As described above, organic resist masks are easier and simpler to use than are silicon oxide masks.

However, it is known that, in the case where organic resist masks are used for silicon material etching, the selectivity of silicon material layers to underlying oxide layers (silicon oxide films) is degraded compared with the case of using silicon oxide masks. The reason is believed to be that by-products from organic resist masks affect etching reactions between oxide underlayers and etchants. Accordingly, in order to improve size precision of the etching process by taking advantage of organic resist masks, it is required to increase the selectivity of silicon material layers to oxide underlayers.

(4) Improvement of Selectivity and Size Precision

A gas mixture in which oxygen gas is added to halide gas can be used as an etchant in order to improve selectivity of silicon material layers to oxide underlayers when organic resist masks are used as described above. However, additive oxygen gas reduces etching selectivity of silicon material layers to organic resist masks. Furthermore, additive oxygen gas increases deposits on sidewalls of organic resist masks, resulting in degradation of size precision.

In the case where an amount of additive oxygen gas in minimized in order to prevent degrading size precision, selectivity of silicon material layers to oxide underlayers remains insufficient. Increasing the amount of additive oxygen gas degrades size precision. Accordingly, there is a trade-off between size precision and selectivity.

In plasma etching of silicon material using organic resist masks in a mixture of halide gas including a halogen such as bromine (Br) and additive oxygen gas, banking deposits are formed on sidewalls of the organic resist masks. The banking deposits degrade size precision as described below.

FIGS. 2A to 2C schematically show steps of plasma etching a substrate (wafer) 300. As shown in FIG. 2A, the substrate 300 includes a silicon substrate 316, a gate insulating film 315 formed on the silicon substrate 316, a silicon material layer 314 such as a polycrystalline silicon film formed on the gate insulating film 315, the silicon material layer 314 being subjected to etching, and a organic resist mask 313 having a predetermined pattern.

Desorption products (silicon halide) which are produced in plasma etching of the polycrystalline silicon film 314 react with oxygen in the plasma at solid surfaces of the substrate 300. These reactions produce dissociated halogen radicals an silicon oxides. The silicon oxides are deposited on the surface of the polycrystalline silicon film 314 other than the portion where the polycrystalline silicon film 314 is bombarded by ions. More specifically, as shown in FIG. 2B, the plasma-produced silicon oxides are deposited on sidewalls 313a of the organic resist meek 313 so as to form banking deposits 317.

The banking deposits 317 serve as an-additional mask to the organic resist mask 313 beyond the original mask pattern of the organic resist mask 313. This causes an insufficient etching of the polycrystalline silicon film 314 beneath the banking deposits 317. As a result, as shown in FIG. 2C, a pattern (profile) of the etched polycrystalline silicon film 314b is shifted from the original pattern of organic resist mask 313, so that the size precision is significantly degraded. Since the influence of banking deposits depend on the resist pattern, patterns is more significant than that of dense resist patterns. This causes line width variations in line patterns. In addition, in the case of bromine-based etchants, deposit amounts of silicon oxide are increased by reactions between silicon bromide and oxygen, since the bond energy of bromine to silicon is lower than that of oxygen.

In order to solve such problems, an amount of oxygen gas may be increased in an additive etching step which is performed after the etching step of silicon material is substantially finished and an oxide underlayer is exposed. Alternatively, oxygen gas may be introduced in the additive etching step. However, practically, deciding a timing for changing the oxygen gas flow rate is difficult. Increasing or adding oxygen gas in the additive etching step causes deviations in resultant patterns of the silicon material layer.

In order to increase selectivity of silicon material layers to resist masks, the etch rate of silicon material layers may be increased by using plasma having a density as high as $10^{12}/cm^3$. In high density plasma, the ionization ratio is increased so as to enhance dissociation of etching-produced products into components, producing radicals which etch silicon material layers. Accordingly, ion-contribution to the etching is enhanced so that the selectivity is improved.

However, high density plasma causes the following problems. Electron build-up in surfaces of the substrates is necessarily increased. Local differences in accumulated electric charge causes insulation breakdown in oxide underlayers. Notches are formed on surfaces of silicon material layers in the etching. In the case where organic resist masks are used, etching-produced by-products including carbon are recombined and polymerized in the plasma and deposited on surfaces of the substrates. In addition, since the dissociation of etching-produced silicon halide is further enhanced in the high density plasma, deposits of silicon oxide on substrates and resist masks are increased. This degrades the size precision as described above. Furthermore, controlling etch rates becomes difficult due to increasing dissociation and deposit reactions.

(5) Low Damage

Additive etching is performed after oxide underlayers are exposed, in order to remove etching residues and to reduce variations in the thickness of silicon material layers due to the etch rate variations. Thus, it is required to improve the selectivity of the silicon material layers to the oxide underlayers, to reduce damage of the oxide underlayer, to prevent oxide underlayers from being overetched to silicon substrates underlying the oxide underlayers, and to prevent the degradation and insulation breakdown of oxide underlayers due to bombardment and electron build-up from the plasma.

(6) Diagnosis and Control of Etching Apparatus and Plasma Condition

Measurements of the etch rates or thicknesses of layers or firms by optical observations or by SEM observations of cross-sections of sample wafers have been used as conventional methods for diagnosing plasma conditions. However, these methods are not only time and labor consuming as described above, but also are subject to influences of the previous fabrication steps. For example, problems in a heating process performed in the step of forming a silicon material layer cause changes in etch rates and etched shapes of the layer, even if the etching apparatus operates normally to provide optimum plasma conditions.

These changes in etch rates and etch shapes are usually considered to be a result of a malfunction of the etching apparatus. However, whether the cause of such changes is due to a malfunction of the etching apparatus or not cannot be diagnosed until the etch, rates or the film thickness are measured again using other wafers. Consequently, measurements of etch rates or film thicknesses are not good indices which exactly represent plasma conditions and operation conditions of the etching apparatus, since these measurements change depending upon not only plasma conditions but also wafer conditions.

In an actual etching process, it is important to control process parameters so as to obtain an optimum plasma condition for etching, such as a condition providing maximum selectivity. For example, in the conventional plasma etching apparatus 200, plasma condition is controlled by maximizing the input power of the microwaves. That is, the plasma etching apparatus 200 adjusts the microwaves to minimize (to zero) the power of reflected waves of the microwaves which travel in the waveguide 202.

However, the minimum (zero) power of the reflected wave does not necessarily correspond to the maximum power of the input waves. In addition, the isolation of the directional coupler 209 of the plasma etching apparatus 200 is not very sufficient. Therefore, the controlling of the microwaves in the waveguide 202 cannot necessarily realize the optimum plasma condition for etching in the vacuum chamber 204.

In the plasma etching apparatus 200, the plasma condition is also controlled by changing current values of the solenoid coils 205 so as to change the magnetic field 206. However, optimum current values of the solenoid coils 205 to realize the optimum plasma condition are varied depending on many factors such as the kinds of etch gases, gas pressures for discharge, the power of the input microwaves, kinds of silicon material to be etched, shapes and sizes of the solenoid coils 205 and reaction chamber 215, and the like. Accordingly, it is required to set electric current values of the solenoid coil 205 for each combination of factors. This makes it difficult to effectively control the plasma condition.

Japanese Laid Open Patent Publication No. 6-188221 describes a method for controlling plasma conditions by detecting emission intensity of the plasma. In this method, stub pins are adjusted so as to make the detected emission intensity maximum in order to generate an efficient plasma condition. However, since a plurality of etch gases are generally used in the conventional plasma etching apparatus 200, reactions in the plasma are so complicated that it is difficult to obtain the optimum plasma condition by maximizing an emission intensity of an active species.

As described above, conventional methods for controlling process parameters to realize the optimum plasma conditions for high selectivity and to estimate an actual selectivity from the current plasma condition in the etching apparatus have many practical problems.

SUMMARY OF THE INVENTION

The dry etching method of the present invention is a method for etching silicon material layers formed on oxide underlayers by using plasma of a gas mixture including halogen and oxygen. The method includes the steps of: measuring intensities of a first emissions from the plasma at a first wavelength and a second emissions from the plasma at a second wavelength: obtaining a ratio of the intensity of the first emissions to that of the second emissions; measuring selectivity of silicon material layers to oxide underlayers for a condition of the plasma for which the emission intensity ratio is obtained; obtaining a correlation between the emission intensity ratio and the selectivity; and setting a plasma condition for a desired selectivity based on a measured emission intensity ratio by using the correlation. In one embodiment of the invention, in the step of measuring intensities, emissions from oxygen radicals and emissions from halogen radicals are measured as the first and second emissions, respectively. Preferably, the gas mixture includes at least one of bromine and chlorine as the halogen.

In the step of measuring intensities, emissions from oxygen radicals at a wavelength of 777 nm and emissions from bromine radicals at a wavelength of 780 nm may be measured.

In the step of measuring intensities, emissions from oxygen radicals at a wavelength of 777 nm and emissions from chlorine radicals at a wavelength of 808 nm may be measured.

In the step of measuring intensities, emissions from transitions between excited quintet states of oxygen radicals and emissions from transitions between exited triplet states of oxygen radicals may measured as the first and second emissions, respectively.

In another embodiment of the present invention, the plasma is generated by electron cyclotron resonance using microwaves in a magnetic field, and the step of measuring selectivity is performed for a plurality of plasma conditions which are obtained by varying at least one of process parameters of input power of the microwaves, values of electric currents of solenoid coils for generating the magnetic field, and gas pressure of electric discharge.

The dry etching method of the present invention is a method for etching silicon material layers formed on oxide underlayers by using organic resist masks in plasma of a gas mixture including halogen and oxygen. The method includes the steps of: measuring intensities of a first emissions from the plasma at a first wavelength and a second emissions from the plasma at a second wavelength; obtaining a ratio of the intensity of the first emissions to that of the second emissions; end controlling a condition of the plasma based on the emission intensity ratio.

In one embodiment of the invention, in the step of measuring intensities, emissions from oxygen radicals and emissions from halogen radicals are measured as the first and second emissions, respectively. Preferably, the gas mixture includes at least one of bromine and chlorine as the halogen. In the step of measuring intensities, emissions from oxygen radicals at a wavelength of 777 nm and emissions from bromine radicals at a wavelength of 780 nm may be measured.

In the step of measuring intensities, emissions from oxygen radicals at a wavelength of 777 nm and emissions from chlorine radicals at a wavelength of 805 nm may be measured.

In the step of measuring intensities, emissions from transitions between excited quintet states of oxygen radicals and emissions from transitions between excited triplet states of oxygen radicals may be measured an the first and second emissions, respectively.

In the step of measuring intensities, emissions at a wavelength of 777 nm from transitions between the excited quintet states of oxygen radicals and emissions at a wavelength of 844 nm from transitions between the excited triplet states of oxygen radicals may be measured.

In the step of measuring intensities, emissions from oxygen ions and emissions from transitions between excited triplet states of oxygen radicals may be measured as the first and second emissions, respectively.

In the step of measuring intensities, emissions at a wavelength of 588 nm from oxygen ions and emissions at a wavelength of 844 nm from transitions between excited triplet states of oxygen radicals may be measured.

In another embodiment of the present invention, the step of measuring intensities includes the steps of: condensing emissions from the plasma: separating first and second light from the condensed emissions according to the first and second wavelengths; and measuring respective intensities of the first and second light.

In still another embodiment of the present invention, the plasma is generated by electron cyclotron resonance using microwaves in a magnetic field, and the step of controlling a condition of the plasma is performed by using at least one of process parameters of input power of the microwaves, values of electric currents of solenoid coils for generating the magnetic field, and gas pressure of electric discharge.

Preferably, in the step of controlling a condition of the plasma, the at least one of process parameters is adjusted so as to increase the emission intensity ratio.

The dry etching apparatus of the present invention is an apparatus for etching silicon material layers formed on oxide underlayers by using organic resist masks in plasma of a gas mixture including halogen and oxygen. The apparatus includes: a chamber in which the plasma is generated; a section for introducing microwaves into the chamber; a unit for generating a magnetic field in the chamber; a system for measuring intensities of a first emissions from the plasma at a first wavelength and a second emissions from the plasma at a second wavelength; a unit for obtaining a ratio of the intensity of the first emissions to that of the second emissions; and a system for controlling a condition of the plasma based on the emission intensity ratio.

Preferably, the system for measuring intensities measures emissions from oxygen radicals and emissions from halogen radicals as the first and second emissions, respectively. Preferably, the gas mixture includes at least one of bromine and chlorine as the halogen.

The system for measuring intensities may measure emissions from oxygen radicals at a wavelength of 777 nm and emissions from bromine radicals at a wavelength of 780 nm.

The system for measuring intensities may measure emissions from oxygen radicals at a wavelength of 777 nm and emissions from chlorine radicals at a wavelength of 808 nm.

The system for measuring intensities may measure emissions from transitions between excited quintet states of oxygen radicals and emissions from transitions between excited triplet states of oxygen radicals as the first and second emissions, respectively.

The system for measuring intensities may measure emissions at a wavelength of 777 nm from transitions between the excited quintet states of oxygen radicals and emissions at a wavelength of 844 nm from transitions between the excited triplet states of oxygen radicals.

The system for measuring intensities may measure emissions from oxygen ions and emissions from transitions between excited triplet states of oxygen radicals as the first and second emissions, respectively.

The system for measuring intensities may measure emissions at a wavelength of 588 nm from oxygen ions and emissions at a wavelength of 844 nm from transitions between excited triplet states of oxygen radicals.

In one embodiment of the present invention, the system for measuring intensities includes; a unit for condensing emissions from the plasma; a unit for separating first and second light from the condensed emissions according to the first and second wavelengths; and a unit for measuring respective intensities of the first and second light.

In another embodiment of the present invention, the controlling system controls the condition of the plasma by using at least one of process parameters of input power of the microwaves, values of electric currents of solenoid coils for generating the magnetic field, and gas pressure of electric discharge.

Preferably, the controlling system adjusts the at least one of process parameters so as to increase the emission intensity ratio.

The method for diagnosing a plasma etching apparatus of the present invention includes the steps of: generating plasma of a gas mixture including halogen and oxygen in a predetermined condition; measuring intensities of a first emissions from the plasma at a first wavelength and a second emissions from the plasma at a second wavelength; obtaining a ratio of the intensity of the first emissions to that of the second emissions; comparing the obtained emission intensity ratio with an emission intensity ratio which is previously measured for the plasma condition when the plasma etching apparatus operates normally.

Preferably, in the step of measuring intensities, emissions from oxygen radicals and emissions from halogen radicals are measured as the first and second emissions, respectively. Preferably, the gas mixture includes at least one of bromine and chlorine as the halogen.

In the step of measuring intensities, emissions from oxygen radicals at a wavelength of 777 nm and emissions from bromine radicals at a wavelength of 780 nm may be measured.

In the step of measuring intensities, emissions from oxygen radicals at a wavelength of 777 nm and emissions from chlorine radicals at a wavelength of 808 nm may be measured.

In one embodiment of the present invention, previous measuring of the emission intensity ratio is performed with respect to process parameters for controlling the plasma condition, and the comparing step includes analyzing the obtained and previously measured emission intensity ratios with respect to the process parameters.

The dry etching method of the present invention is a method for etching silicon material layers formed on oxide underlayers by using a gas mixture including halogen/halide gas and oxygen gas. The method includes the steps of: generating a magnetic field and introducing microwaves for producing plasma of the gas mixture; introducing the oxygen gas into a first region of the magnetic field so as to produce plasma of oxygen gas; and introducing the halogen/halide gas into a second region of the magnetic field which is different from the first region. The oxygen gas is excited in the first region into plasma having an energy level higher than that of plasma of halogen/halide gas excited in the second region.

In one embodiment of the present invention, in the step of generating a magnetic field, the magnetic field is generated so that a resonance region having an intensity of electron cyclotron resonance is formed between the first and second regions, the first region having an intensity stronger then that of the resonance region, and the second region having an intensity weaker than that of the resonance region.

Preferably, one of monocrystalline silicon, amorphous silicon, polycrystalline silicon which is doped with impurity, and polycrystalline silicon without impurity is used as the silicon material.

Preferably, the halogen/halide gas includes at least one of hydrogen bromide and chlorine.

The dry etching apparatus of the present invention is an apparatus for etching silicon material layers formed on oxide underlayers by using plasma of a gas mixture including halogen and oxygen. The apparatus includes: a chamber in which the plasma is generated; a section for introducing microwaves into the chamber; a unit for generating a magnetic field in the chamber; a first gas inlet for introducing oxygen gas into a first region of the magnetic field; and a second gas inlet for introducing halogen/halide gas into a second region of the magnetic field which is different from the first region, The oxygen gas is excited in the first region into plasma having an energy level higher than that of plasma of halogen/halide gas excited in the second region.

In one embodiment of the present invention, the unit for generating a magnetic field generates the magnetic field so that a resonance region having an intensity of electron cyclotron resonance is formed between the first and second regions, the first region having an intensity stronger than that of the resonance region, and the second region having an intensity weaker than that of the resonance region.

Preferably, one of monocrystalline silicon, amorphous silicon, polycrystalline silicon which is doped with impurity, and polycrystalline silicon without impurity are used for etching.

Preferably, the halogen/halide gas includes at least one of hydrogen bromide and chlorine.

Thus, the present invention described herein makes possible the advantages of (1) providing a dry etching apparatus and method for efficiently measuring and estimating selectivity which is obtained in a plasma condition and for controlling the plasma condition so as to realize optimum etching, (2) providing a dry etching apparatus and method in which selectivity of silicon material layers to oxide underlayers and selectivity of silicon material layers to resist masks are both improved, and in which damage to oxide underlayers is lowered, (3) providing a dry etching apparatus and method for realizing high size precision by reducing size variations in the etching, and (4) providing a method for diagnosing a plasma condition in the etching process and for diagnosing operation malfunctions of a dry etching apparatus.

These and other advantages of the present invention will become apparent to those skilled in the art upon reading and understanding the following detailed description with reference to the accompanying figures.

BRIEF DESCRIPTION OF THE DRAWINGS

FIG. 12A is a diagram illustrating an exemplary change in the emission intensity ratio of oxygen to bromine when current values of the solenoid coils are controlled.

FIG. 12B is a diagram illustrating an exemplary change in the selectivity of a polycrystalline silicon layer to an oxide underlayer when current values of the solenoid coils are controlled, corresponding to FIG. 12A.

FIG. 12C is a diagram illustrating an exemplary change in uniformity of the etch rate in a wafer when current values of the solenoid coils are controlled, corresponding to FIG. 12A.

FIG. 13 is a diagram illustrating the relationship between the selectivity of polycrystalline silicon layers to oxide underlayers and the emission intensity ratio of light having a wavelength of 777 nm to light having a wavelength of 844 nm.

FIG. 14 is a diagram illustrating the relationship between the selectivity of polycrystalline silicon layers to resist masks and the emission intensity ratio of light having a wavelength of 777 nm to light having a wavelength of 844 nm.

FIG. 21 is a diagram schematically illustrating an example of controlling the etching condition according to the present invention.

DESCRIPTION OF THE PREFERRED EMBODIMENTS

Hereinafter, the present invention will be described by way of illustrative examples with reference to the accompanying drawings.

EXAMPLE 1

First, basic principles of the first example of this invention will be described. In this example, a method is described for measuring selectivity of the silicon etching in which silicon material layers formed on oxide underlayers of silicon oxide are etched using an etchant gas mixture of halogen and/or halide (halogen/halide) gas and additive oxygen gas. A method for estimating the selectivity obtained in the plasma is also described in this example.

Selectivity is dependent upon the density of oxygen gas in the plasma of the gas mixture including halogen and oxygen, for oxygen radicals significantly contribute to the selectivity. Since dissociation energy of oxygen is higher than that of halogen, oxygen radical density depends on the plasma density or electron density. As a result, even at the same oxygen gas density, the oxygen radical density is relatively high in a region where the plasma density or electron density is high. Consequently, by measuring the relative intensity of the emission from the oxygen radicals, which presumably indicates the oxygen radical density, the selectivity can be estimated effectively.

When a malfunction occurs in a plasma etching apparatus, electron density in the plasma is changed by the malfunction of the plasma etching apparatus. Because emission intensity depends on the electron density, malfunctioning of the etching apparatus can be detected by monitoring the emission intensity. In addition, uniformity of the plasma can be evaluated by measuring the emission intensity of the plasma.

Figure 1:
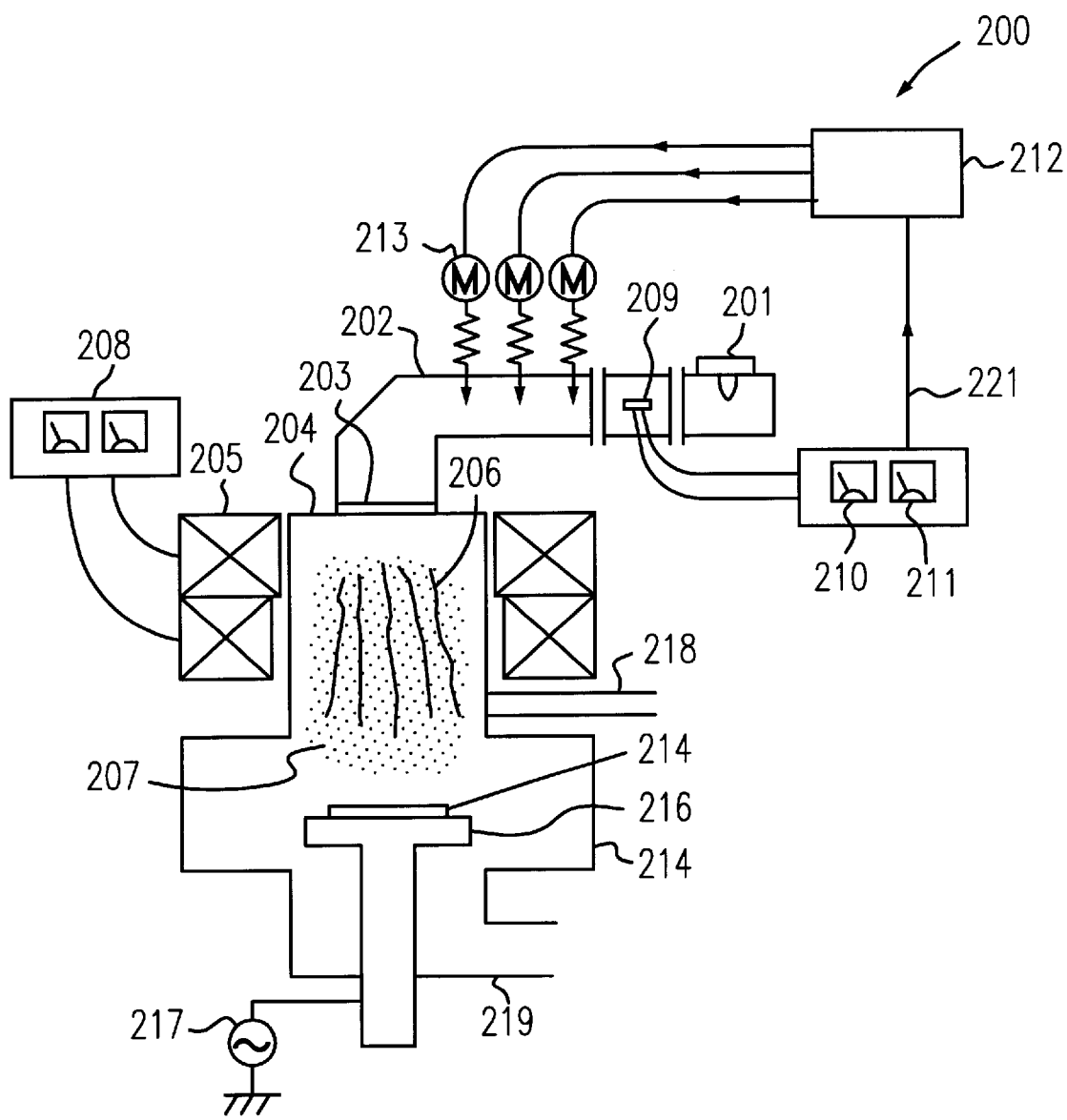
FIG. 1 is a schematic view of a conventional ECR plasma etching apparatus.
Figure 2A:
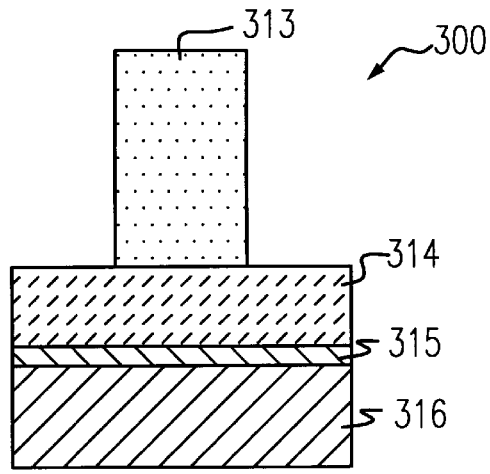
FIGS. 2A to 2C are cross-sectional diagrams illustrating the steps of polycrystalline silicon etching using a conventional dry etching apparatus and method.
Figure 2B:
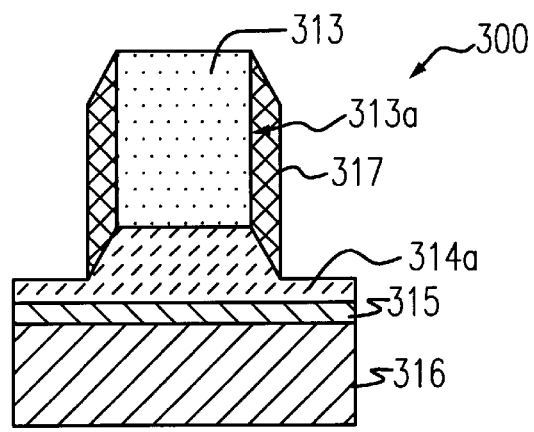
Figure 2C:
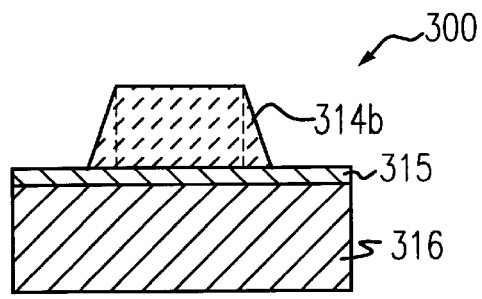
Figure 3:
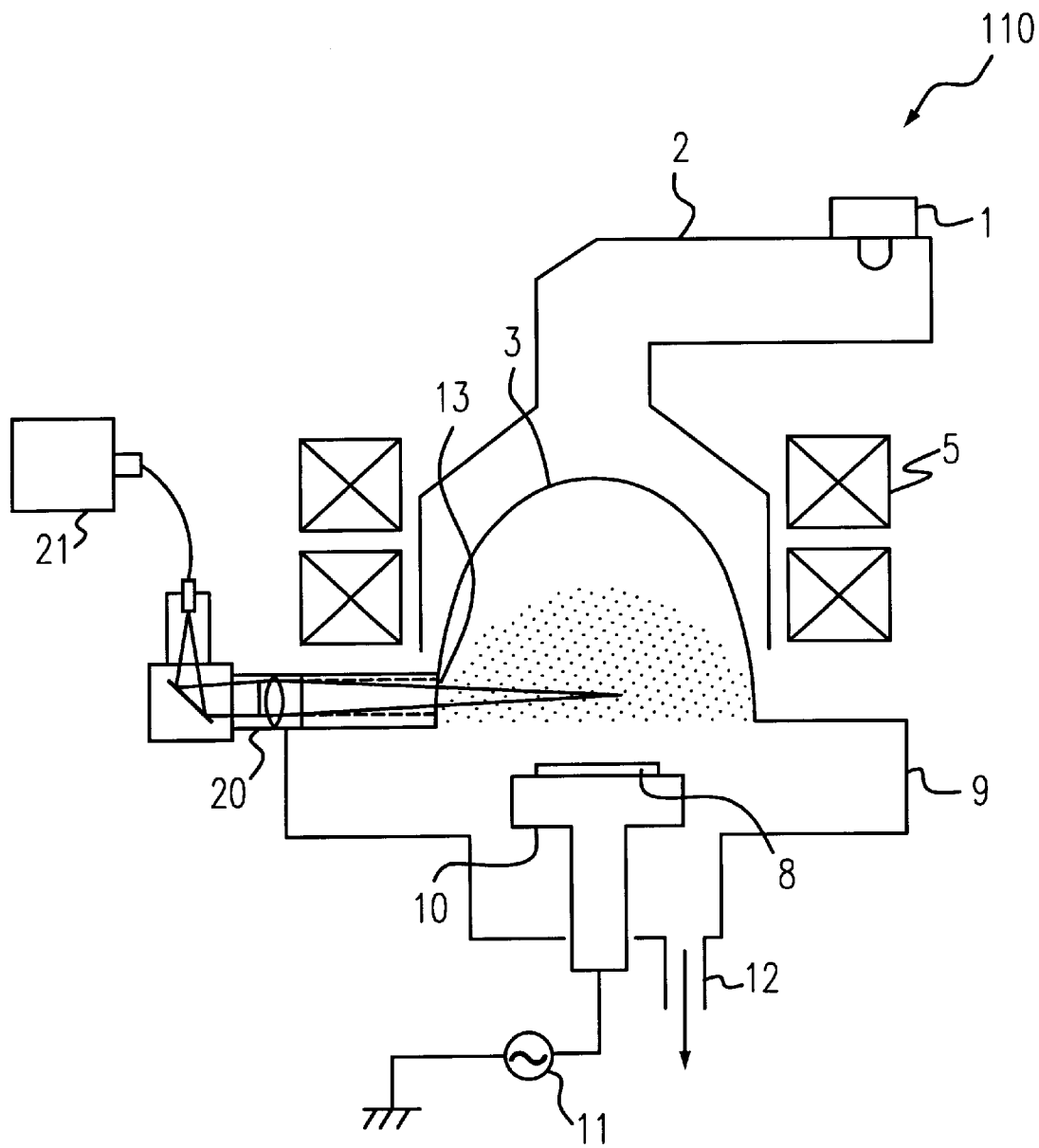
FIG. 3 is a partial schematic view of a plasma etching apparatus including a part for measuring selectivity according to one example of the present invention.

FIG. 3 schematically shows a cross-sectional view of an ECR plasma etching apparatus 110 according to one example of the present invention. As shown in FIG. 3, the ECR plasma etching apparatus 110 includes a magnetron 1 for generating microwaves at 2.45 GHz, for example, a waveguide 2 for transferring the microwaves into a vacuum chamber 3 in which the plasma is generated, solenoid coils 5 provided around the vacuum chamber 3 for generating a magnetic field in the vacuum chamber 3, and a reaction chamber 9 in which etching processes are performed. The solenoid coils 5 generate the magnetic field so that the magnetic field satisfies the ECR condition.

As shown in FIG. 3, the vacuum chamber 3 has a window 13. An optical system 20 is coupled to the window 13 so as to receive emissions from the plasma in the vacuum chamber 3. The optical system 20 can be implemented by a lens system. The received emissions are directed to an emission spectrometer 21, and are dispersed according to the wavelengths thereof. Intensities of the dispersed emissions are detected by an area sensor (not shown) using a CCD. In this example, the ratio of intensities of the emissions is calculated based on the peak emission wavelengths.

The plasma gas which is ECR-excited in the vacuum chamber 3 is transported to a reaction chamber 9 along the magnetic flux of the magnetic field generated by the solenoid coils 5. A wafer platen electrode 10 for holding a wafer B to be etched is provided in the reaction chamber 9. The wafer platen electrode 10 is connected to a high frequency power supply 11 for supplying a high frequency bias voltage. The reaction chamber 9 is provided with a gas exhaust 12 to which is coupled a vacuum exhaust system such as a turbo molecular pump having a large exhaust rate.

In FIG. 3, a control system for the ECR plasma etching apparatus 110 is not shown, though the ECR plasma etching apparatus 110 comprises such a control system for ECR plasma etching apparatus 130 shown in FIG. 9, as will be described in Example 2. Power of microwaves from the magnetron 1, electric currents of the solenoid coils 5, RF power from the high frequency power supply 11, gas pressure for electric discharge in the vacuum chamber 3, and the like are monitored and controlled by the control system. Emission intensity ratios are calculated from emission intensities obtained via the emission spectrometer 21 and the area sensor, by a microprocessor or the like included in the control system.

Next, measurement of the emission intensity ratio and estimation of the selectivity of the ECR plasma etching apparatus 110 will be described.

In this example, polycrystalline silicon layers are etched being organic resist masks by an etchant gas mixture of hydrogen bromide, chlorine, and oxygen. The emission intensity ratio of oxygen radicals to bromine radicals is measured by varying process parameters of the ECR plasma etching apparatus 110 such as pressure, magnetic field, RF power from the high frequency power supply 11, power of the microwaves from the magnetron 1, gas flow rate, mixture ratio of the gas mixture, and the like. In order to obtain the intensity ratio (O/Br), respective intensity peaks of emissions having a wavelength of 777 nm (oxygen radical) and emissions having a wavelength of 780 nm (bromine radicals) are measured.

Such peaks are measured by the emission spectrometer 21 which is specifically designed to detect peaks in a frequency band including such wavelengths via emissions received through the optical system 20. Intensities of the detected peaks are measured by using a conventional method such as using a CCD.

Figure 4:
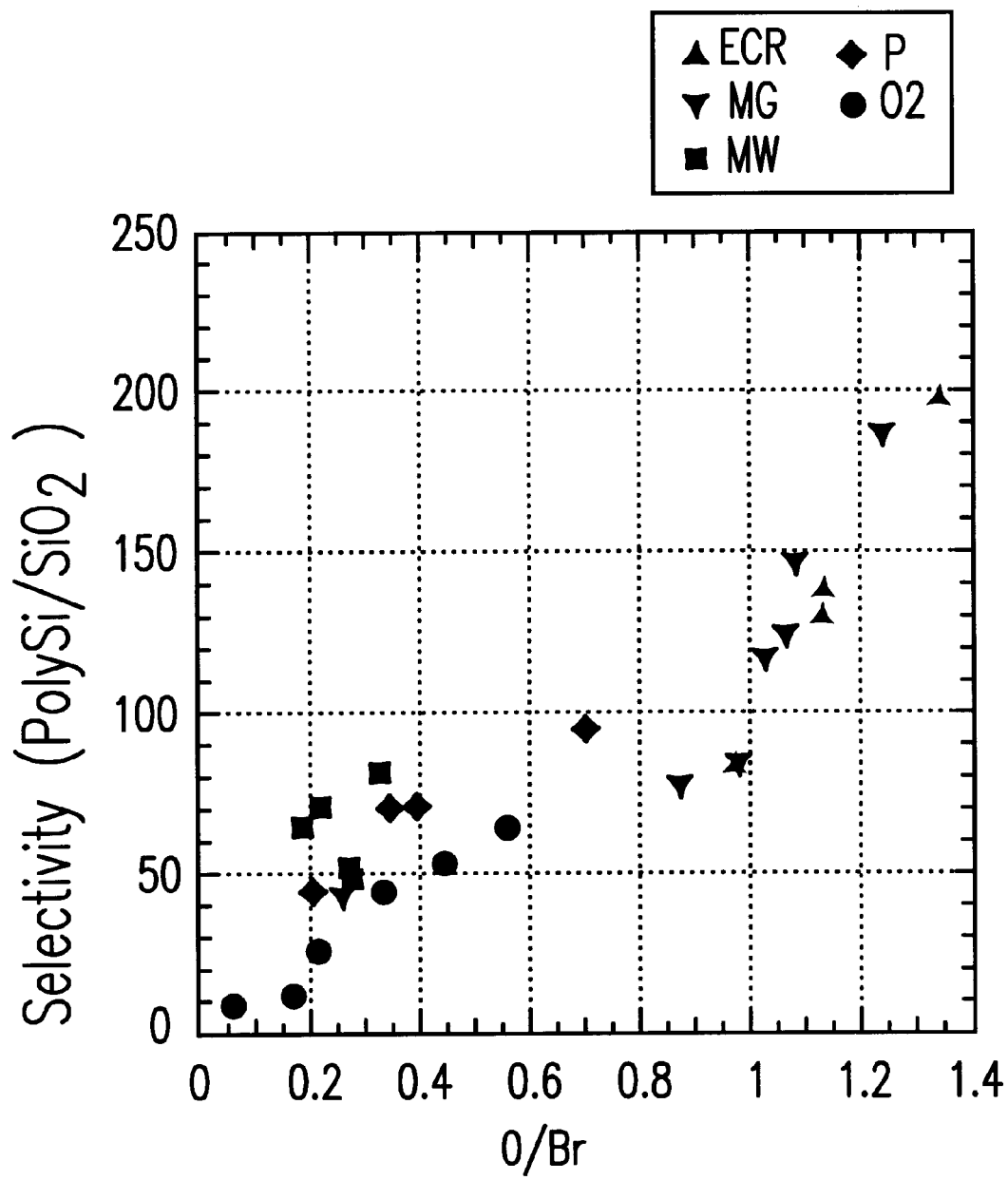
FIG. 4 is a diagram illustrating the relationship between the selectivity and the ratio of emission intensities (oxygen/bromine).

FIG. 4 shows exemplary results of such measurements. In FIG. 4, the ordinate denotes the selectivity of polycrystalline silicon layers to oxide underlayers, and the abscissa denotes the emission intensity ratio of oxygen radicals to bromine radicals (O/Br). The selectivity is obtained by measuring etch rates using respective wafers for polycrystalline silicon layers and silicon oxide layers, by varying process parameters.

In each of the wafers for measuring etch rates of polycrystalline silicon layers, a silicon oxide film having a thickness of about 100 nm is formed on a silicon substrate by thermal oxidation, and a polycrystalline silicon film having a thickness of about 500 nm is formed on the silicon oxide film by CVD method. In each of the wafers for measuring etch rates of silicon oxide layers, a silicon oxide film having a thickness of about 500 nm is formed on a silicon substrate by thermal oxidation.

The etching process is performed for one minute for the polycrystalline silicon wafers, and two minutes for the silicon oxide wafers. Changes in the thickness of the films before and after the etching are measured and etch rates are measured. The selectivity is obtained by dividing the etch rate of polycrystalline silicon by that of silicon oxide.

In FIG. 4, triangles (▲) represent results obtained by varying a height of the ECR region of the magnetic field (at an intensity of 875 G) with respect to the wafers from 110 mm to 200 mm. Diamonds (♦) represent results obtained by varying gas pressure from 0.07 Pa to 3 Pa, inverted triangles (▼) represent results obtained by varying a gradient of the magnetic field in the ECR region from 30 G/cm to 70 G/cm, solid circles (●) represent results obtained by varying oxygen gas flow from 0 sccm to 10 sccm, and squares (■) represent results obtained by varying power of the microwaves from 700 W to 1200 W.

As shown in FIG. 4, the selectivity and emission intensity ratio (O/Br) exhibit a relatively strong correlation with respect to all the process parameters that were considered. Therefore, by measuring previously the selectivity at several measurement points so as to obtain the correlation, the selectivity of the plasma etching can be efficiently estimated by the measured value of the emission intensity ratio of the plasma. Since a value of the selectivity required for an etching process is one greater than a predetermined value, but not an exact value, the correlation shown in FIG. 4 is sufficient in order to set the etching conditions to obtain the selectivity which is practically required.

In this example, measurements of the selectivity of etching polycrystalline silicon as silicon material was explained, though, the selectivity of amorphous silicon and monocrystalline silicon is also measured in the same way. In the case where silicon material is doped with impurities, though the exact values of selectivity are different, similar correlation is obtained.

As described above, the selectivity and the emission intensity ratio (O/Br) exhibit substantially the same correlation with respect to all the process parameters. Therefore, the number of process parameters for controlling the plasma condition is not limited to one in order to obtain optimum selectivity. Rather preferred process parameters can be used which are selected from a plurality of process parameters. Thus, according to the invention, the selectivity can be optimized even when variable process parameters are restricted by hardware of the etching apparatus, and when process parameters are not independent of each other. In addition, the selectivity can also be optimized when ranges of the variable process parameters are limited as in the case of RIE apparatus.

In this example, the wavelengths of 777 nm and 780 nm are used for measuring the emission intensity of oxygen radicals and bromine radicals, respectively. These two wavelengths have the following advantages: Emissions having these wavelengths are relatively immune to noise from emissions of other wavelengths, and can be detected at the same time by an emission spectrometer using a CCD since the wavelengths are close. However, wavelengths for such measurements are not limited to these two. Any wavelengths of emissions from oxygen radicals and bromine radicals can be chosen. For example, in the case where emission intensities are measured by devices using filters, it is preferable to use two wavelengths which are much different from each other, such as wavelengths of 777 nm from oxygen radicals and 808 nm from chlorine radicals.

Figure 5:
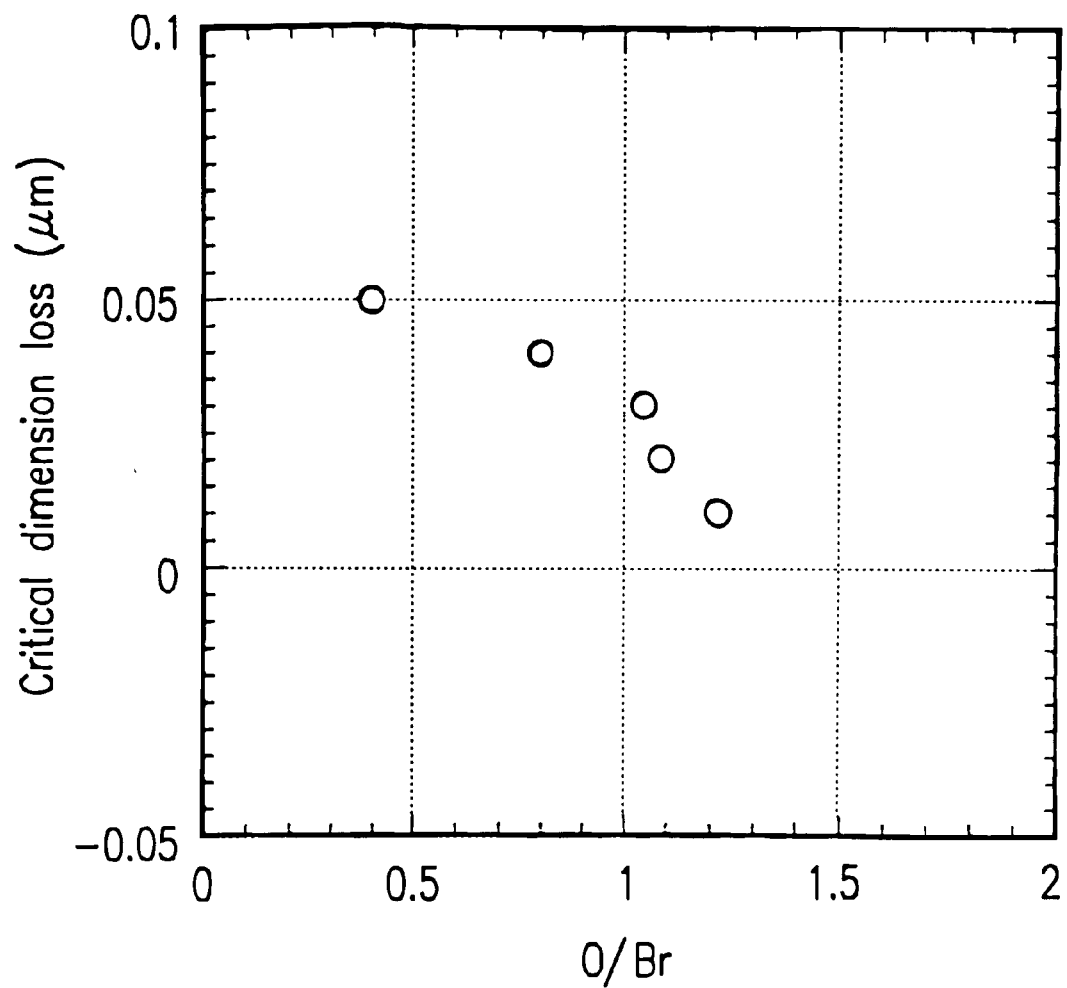
FIG. 5 is a diagram illustrating the relationship between the etch bias (critical dimension loss) and the ratio of emission intensities (oxygen/bromine).

Next, the relationship between process etch bias and selectivity will be explained. FIG. 5 shows the relationship between process etch bias and selectivity obtained under the same measurement conditions using the same process parameters as those of FIG. 4. FIG. 5 shows results which are obtained by etching polycrystalline silicon film having a thickness of 150 nm using organic resist masks so as to pattern into line electrodes having a linewidth of 0.25 $\mu$m through photolithography processes.

In FIG. 5, the ordinate denotes critical dimension lose as the process etch bias. The critical dimension loss is obtained by measuring linewidths of organic resist masks before the etching and linewidths of patterned polycrystalline silicon films after the organic resist masks are stripped, by using a measuring SEM. The critical dimension loss is expressed by the difference between the measured linewidths before and after the etching. The abscissa denotes the emission intensity ratio (O/Br) obtained under each etching condition (set of process parameters).

As shown in FIG. 5, the process etch bias (critical dimension loss) is minimized to almost zero when the emission intensity ratio (O/Br) is greater than a certain value. The process etch bias is caused mainly by banking deposits on sidewalls of resist masks during the etching process. Accordingly, by controlling the plasma condition to increase the emission intensity ratio higher then a certain value, the sidewall deposits can be prevented. That is, problems due to the sidewall deposits of the resist masks such as linewidth variation, which depends on line density of patterns, can be avoided by controlling the plasma condition to increase the emission intensity.

Next, an application of the method of measuring and estimating selectivity of the present invention to a conventional helicon etcher will be described. Measurements of etch rates are performed by using respective wafers for polycrystalline silicon and silicon oxide and by varying process parameters. The wafers are prepared in the same manner as those for the ECR plasma etching apparatus 110, as described above. In this case, respective intensities of the emissions having a wavelength of 777 nm and the emissions having a wavelength of 808 nm are measured by using an emission spectrometer utilizing filters, so as to obtain the emission intensity ratio. Chlorine gas is used as a halogen gas etchant. In the helicon etcher, variable process parameters are gas pressure and power of the helicon waves.

Figure 6:
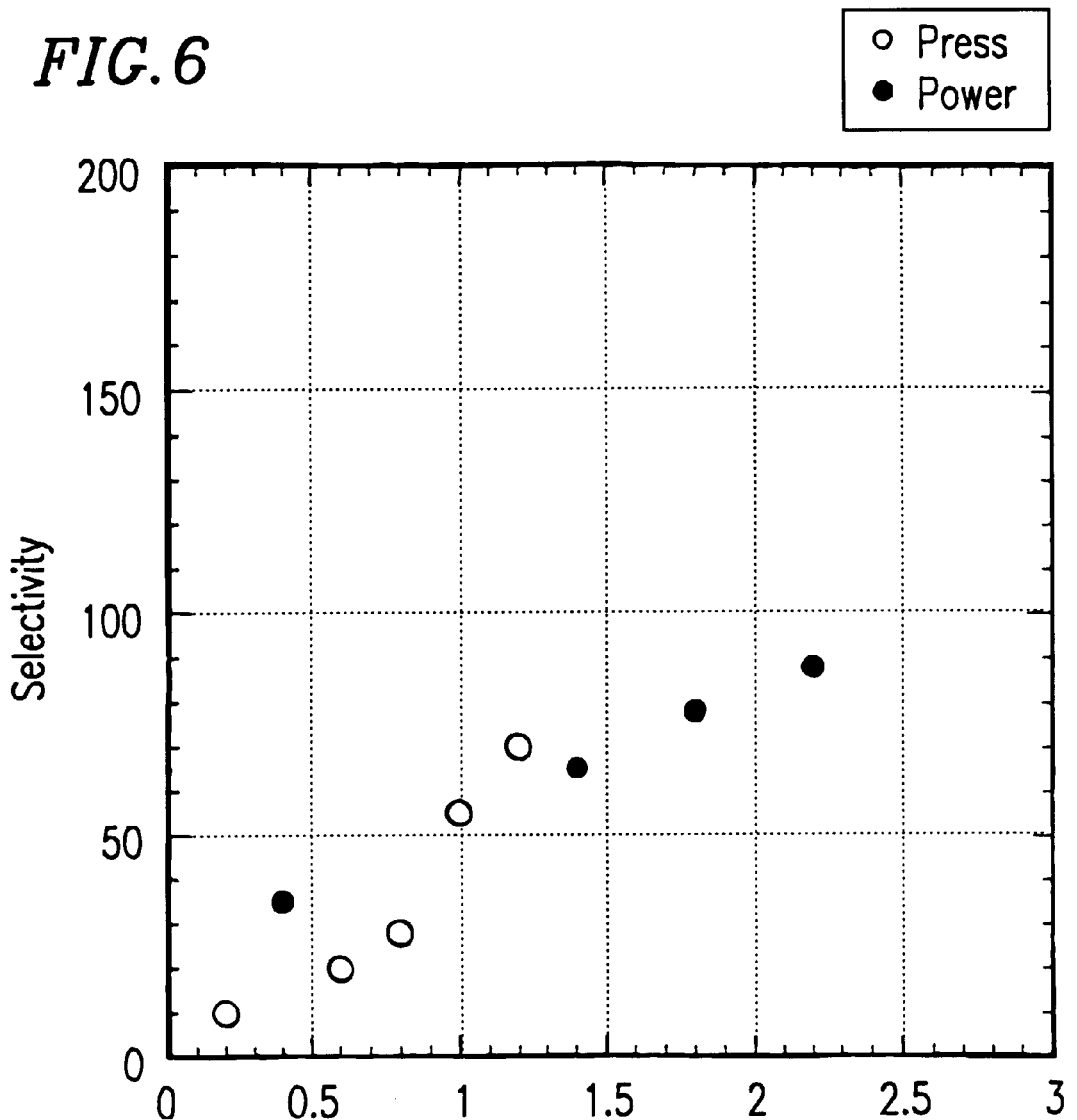
FIG. 6 is a diagram illustrating the relationship between the selectivity and the ratio of emission intensities (oxygen/chlorine) obtained by using a helicon etcher.

FIG. 6 shows results of the measurements using the helicon etcher. In FIG. 6, the ordinate denotes the selectivity of polycrystalline silicon layers to oxide underlayers, and the abscissa denotes the emission intensity ratio of oxygen radicals to chlorine radicals (O/Cl). In FIG. 6. circles (○) represent results obtained by varying gas pressure, and solid circles (●) represent results obtained by varying power of the helicon waves.

As shown in FIG. 6, the selectivity and emission intensity ratio (O/Cl) exhibit a positive correlation with respect to these process parameters. Therefore, according to the present invention, by previously measuring the selectivity at several measurement points so as to obtain the correlation, the selectivity of the plasma etching can be efficiently estimated from the measured value of the emission intensity ratio of the plasma for helicon etchers as well as ECR plasma etchers.

Next, evaluation of uniformity of the plasma using the method of measuring the emission intensity ratio of the present invention will be described. Uniformity of the plasma is one important factor to realize uniform (i.e., reproducible vertical and lateral) etching across the wafer or all surfaces within a batch.

Figure 7A:
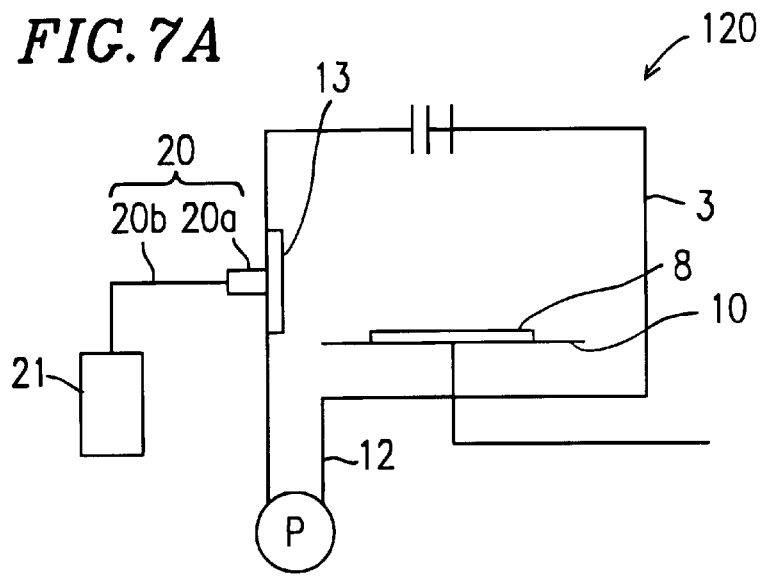
FIGS. 7A and 7B are a schematic side and a plan view of a part of the plasma etching apparatus for measuring uniformity of the plasma according to the present invention, respectively.
Figure 7B:
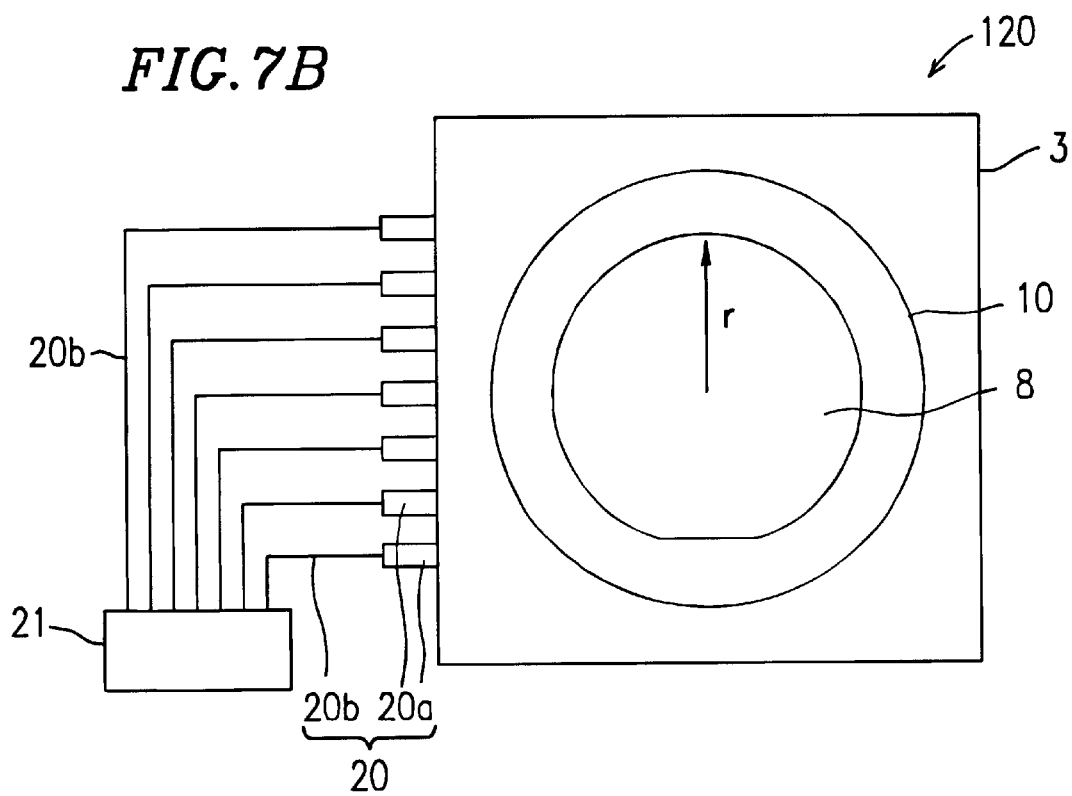

FIG. 7A schematically shows a side view of a plasma etching apparatus 120 in which uniformity of the plasma is observed according to the present invention. FIG. 7B schematically shows a plan view of the plasma etching apparatus 120. In FIGS. 7A and 7B, the components of the plasma etching apparatus 120 which are the same as those of the ECR plasma etching apparatus 110 are denoted by the same numerical numbers.

FIGS. 7A and 7B show a part of the plasma etching apparatus 120 in order to demonstrate measuring the emission intensity ratio and uniformity of the plasma. The plasma etching apparatus 120 also includes, though not shown, units for generating and transferring microwaves, units for generating magnetic field, units for introducing etching gas, units for supplying RF power, and a control system for monitoring and controlling all the units, as in the case of the ECR plasma etching apparatus 110 shown in FIG. 3 or ECR plasma etching apparatus 130 shown in FIG. 9.

As shown in FIGS. 7A and 7B, the optical system is coupled to a window 13 provided the a vacuum chamber 3. The optical system 20 includes a plurality of optical units 20a such as condensing lenses and optical waveguides 20b such as optical fibers. The optical units 20a are provided at the plurality of positions of the window 13 so as to detect emissions from different regions of the plasma in the vacuum chamber 3.

Preferably, the optical units 20a are placed so as to cover all areas of a wafer stage 10 where a wafer 8 is loaded.

Each of the optical units 20a detects emissions from the corresponding region of the plasma, and the corresponding optical waveguide 20b transmits light of the emissions to an emission spectrometer 21. By using the emission spectrometer 21, intensities of the emissions having predetermined wavelengths, for example, emissions from oxygen radicals and those from halogen radicals, are measured for each region of the plasma corresponding to the respective optical unit 20a. Thus, the emission intensity ration are obtained for a plurality of regions of the plasma. The uniformity of the plasma is evaluated by comparing the emission intensity ratios over the regions.

Figure 8:
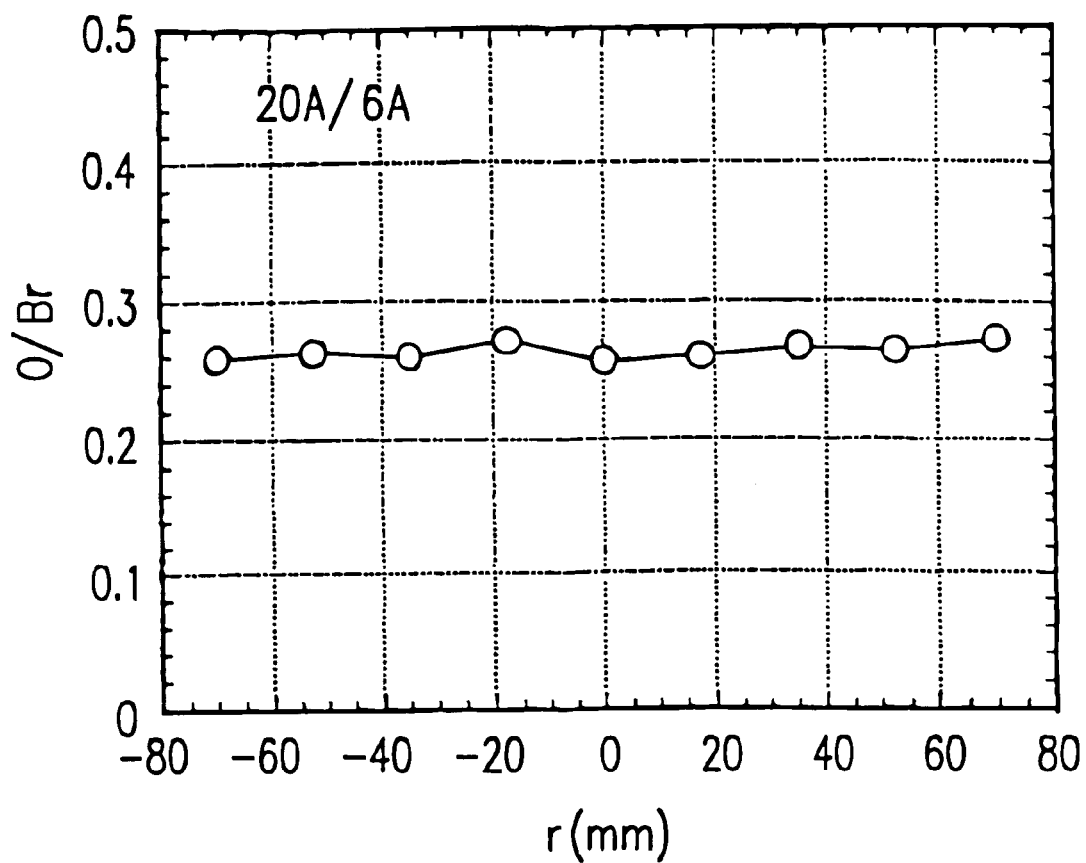
FIG. 8 is a diagram illustrating results of a measurement of emission intensity ratios of oxygen to bromine along a diameter of a wafer.

FIG. 8 shows an example of results obtained from the above measurements using the plasma etching apparatus 120. Emissions from the plasma at a height of 100 mm from the wafer 8 are measured to calculate the emission intensity ratios along the diameter direction of the wafer 8.

In FIG. 8, the ordinate denotes the emission intensity ratio of oxygen radicals to bromine radicals (O/Br), and the abscissa denotes position in a wafer along the diameter r thereof (shown in FIG. 7B). FIG. 8 exhibits substantially constant emission intensity ratios over the wafer, which are obtained from the plasma having a good uniformity.

The intensities of the emissions themselves cannot exactly represent plasma conditions such as the uniformity of the plasma since an absolute value of the emission intensity depends on a shape of the plasma, a measurement distance from a optical unit, and the like. However, a relative intensity, i.e., the ratio of intensities of two emissions having different wavelengths, can represent relatively exact conditions because influences of shape, distance and the like can be off set by using the ratio. Accordingly, as shown in FIG. 8, uniformity of the plasma can be evaluated with sufficient accuracy by measuring the emission intensity ratio.

As described above, since conditions of the plasma can be well-represented by the emission intensity ratio, the plasma conditions such as selectivity and uniformity are well controlled by measuring the emission intensity ratio according to the present invention.

According to this example of the present invention, selectivity and uniformity of the plasma can be measured prior to etching target wafers. In addition, according to this example of the present invention, the emission intensity ratio can be monitored during the etching. If the emission intensity ratio is drops below a predetermined value as determined by the above mentioned method, a process parameter is adjusted such as pressure, RF power, power of microwaves, etc, so as to hold the emission intensity ratio (i.e., the corresponding selectivity) of the plasma at the predefined value. Controlling plasma conditions will be discussed in detail in the following examples.

EXAMPLE 2

In this example, controlling plasma conditions in a plasma etching apparatus 130 of the present invention will be described. In the plasma etching apparatus 130, silicon material layers formed on oxide underlayers (silicon oxide) are etched by using organic resist masks in plasma from a gas mixture including halogen and/or halide gas and oxygen gas. In this example, the intensity ratio of two emissions having different wavelengths (first and second wavelengths) which respectively represent specific elements included in the gas mixture is measured. Plasma conditions for the etching are controlled based on the emission intensity ratio.

Figure 9:
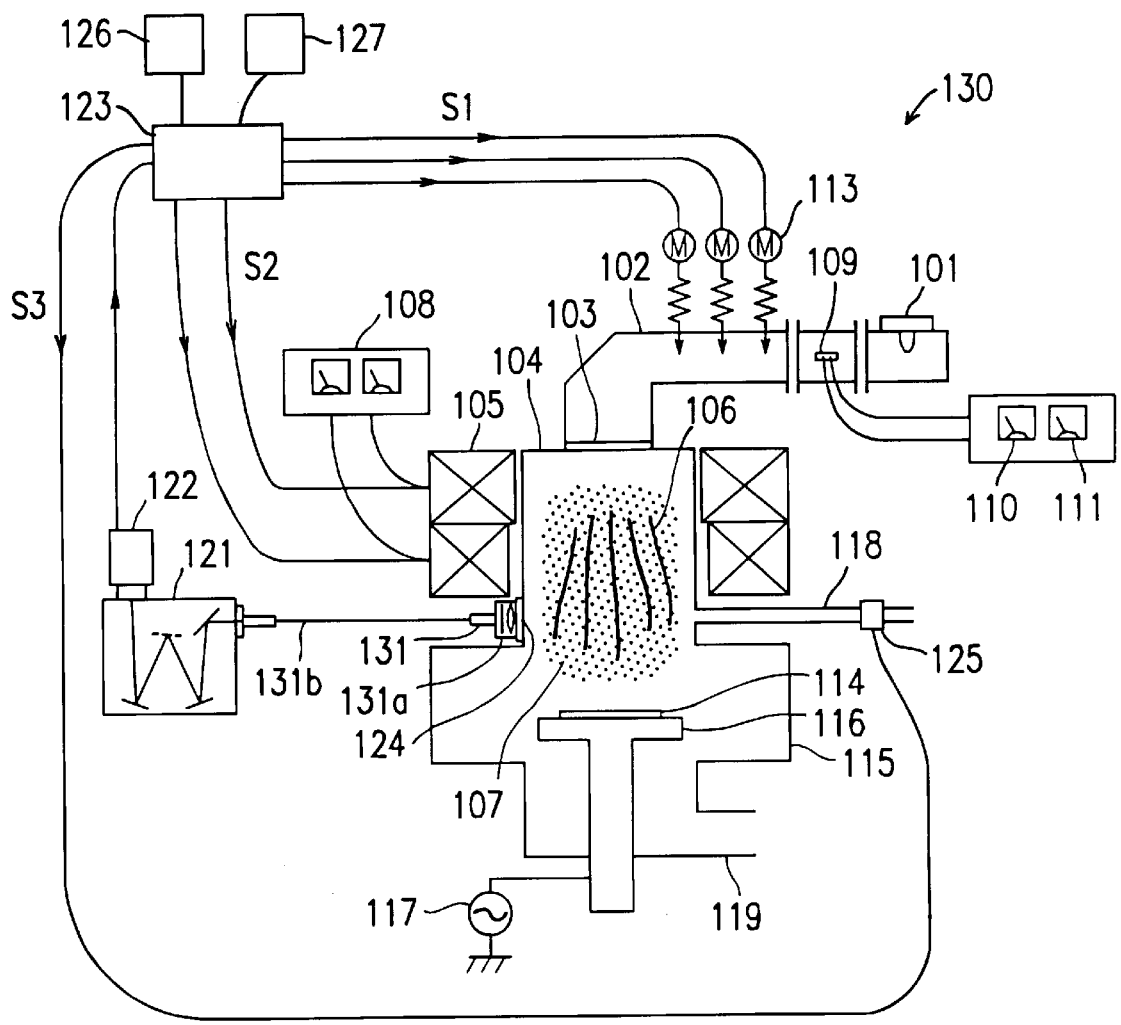
FIG. 9 is a schematic view of an ECR plasma etching apparatus of the present invention.

FIG. 9 schematically shows a cross-sectional view of an ECR plasma etching apparatus 130 of this second example according to the present invention. As shown in FIG. 9, the ECR plasma etching apparatus 130 includes a magnetron 101 for generating microwaves at 2.45 GHz, a waveguide 102 for introducing the microwaves into a vacuum chamber 104 in which the plasma is generated, solenoid coils 105 provided around the vacuum chamber 104, and a reaction chamber 115 in which etching processes are performed.

The microwaves generated by the magnetron 101 are guided by the waveguide 102 into the vacuum chamber 104 through a window 103 made of material such as silica glass which transmits the microwaves. The solenoid coils 105 generate a magnetic field 106 in the vacuum chamber 104. Process gas is introduced from a gas inlet 118 into the vacuum chamber 104. The plasma 107 is generated by cyclotron motion of electrons, the cyclotron motion being caused by multiplier effect of the magnetic field 106 and the electric field of the microwaves.

The solenoid coils 105 are usually divided into at least two coils in order to increase uniformity of the plasma and controllability of the plasma. An ammeter 108 is connected to the solenoid coils 105 so as to detect the electric currents of the solenoid coils 105. A control circuit 123 is also connected to the solenoid coils 105. The control circuit 123 varies independently the electric current values of the respective coils of the solenoid coils 105 so as to change a position of an ECR region having a magnetic field intensity of 875 Gauss and gradient of the magnetic field 106, whereby efficiency of the microwave power and density distribution of the plasma 107 are changed.

A directional coupler 109 and stub pins 113 are provided in the waveguide 102. The directional coupler 109 detects incident wave and reflected wave of the microwaves traveling through the waveguide 102. Intensities of the detected incident wave and reflected wave are indicated by power meters 110 and 111, respectively. The stub pins 113 are connected to the control circuit 123.

A wafer platen electrode (wafer stage) 116 for loading a wafer 114 to be etched is provided in the reaction chamber 115. The wafer platen electrode 116 is connected to a high frequency power supply 117 and is supplied with a high frequency bias voltage. The reaction chamber 115 is provided with a gas exhaust 119 to which a vacuum exhaust system (not shown) such as a turbo molecular pump having a large exhaust rate is coupled.

As shown in FIG. 9, the ECR plasma etching apparatus 130 of the present example further includes an optical system 131 for measuring and analyzing emissions from the plasma 107 in the vacuum chamber 104, an emission spectrometer 121, and an area sensor 122. The optical system 131 can be implemented by utilizing an optical lens system 131a for condensing emissions from the plasma 107 and an optical fiber 131b for guiding the emissions to the emission spectrometer 121.

The optical system 131 is coupled to a window 124 provided in the vacuum chamber 104. The emissions are received and condensed by the optical lens system 131a, and transmitted via the optical fiber 131b to the emission spectrometer 121. The emission spectrometer 121 is specifically designed to detect peaks in a frequency band including such wavelengths via emissions received through the optical system 131. The emission spectrometer 121 separates the emissions according to wavelengths thereof. The separated emissions are detected by a CCD (not shown) in the area sensor 122 and the respective intensities of the emissions are measured.

The control circuit 123 calculates the emission intensity ratios of the plasma in the vacuum chamber 104 from the emission intensities supplied from the area sensor 122. The control circuit 123 generates a signal S1 for controlling insert positions of the stub pins 113, a signal S2 for controlling values of electric currents of the solenoid coils 105, and a signal S3 for controlling pressure of the electric discharge via a pressure control unit 125. The control circuit 123 controls respective units of the ECR plasma etching apparatus 130 by the control signals S1–S3 so as to optimize a condition of the plasma 107 in the vacuum chamber 104.

Next, an etching method using the ECR plasma etching apparatus 130 will be described below. In this example, polycrystalline silicon layers including no impurities are patterned into gate electrodes by etching. A gas mixture of hydrogen bromide, chlorine, and additive oxygen gases is used as a process gas. Respective wavelengths representing the emissions from oxygen radicals (first wavelength) and bromine radicals (second wavelength) are measured in order to obtain the emission intensity ratios.

Figure 10:
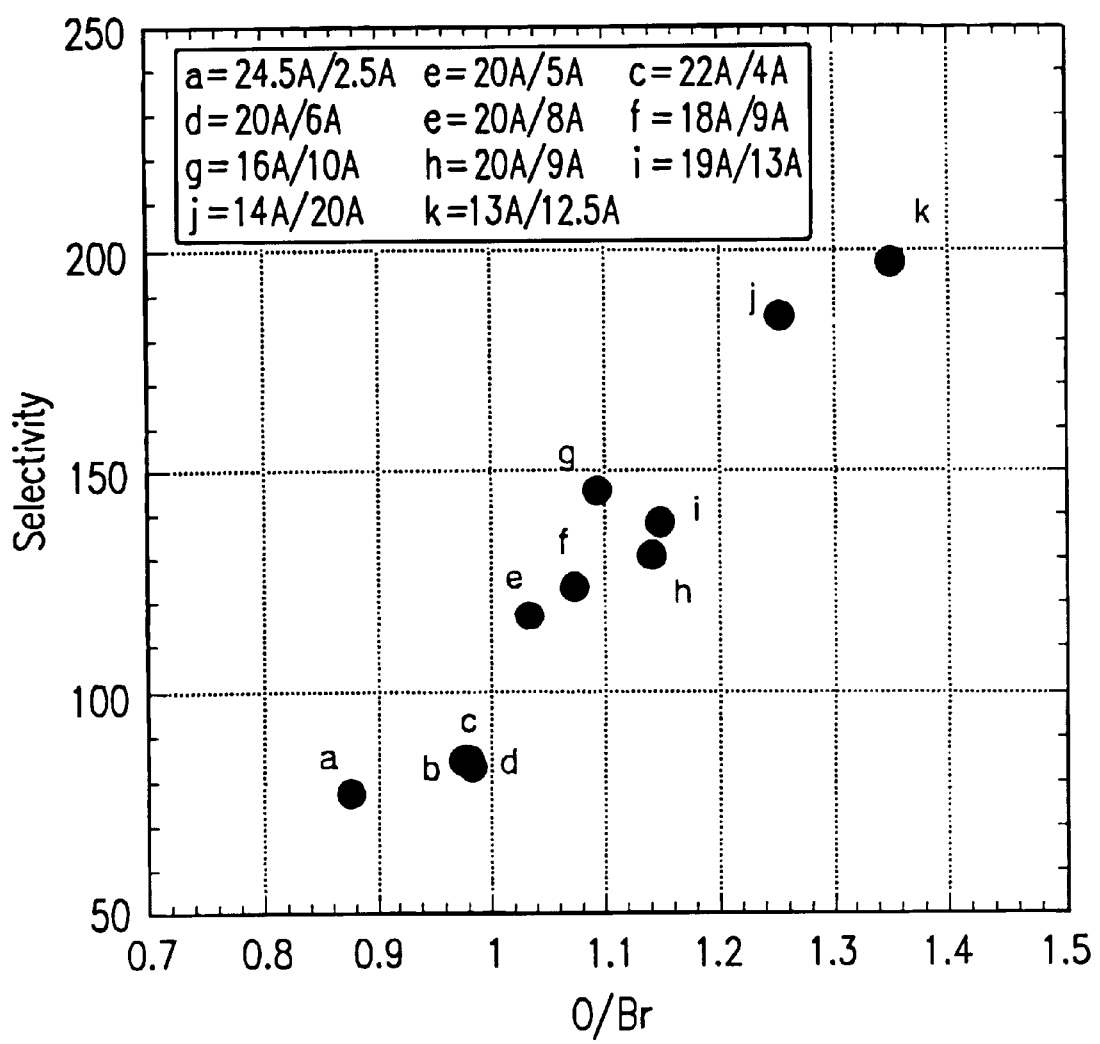
FIG. 10 is a diagram illustrating the relationship between the selectivity of polycrystalline silicon layers to oxide underlayers and the emission intensity ratio of oxygen to bromine obtained by the present invention.

FIG. 10 shows the relationship between selectivity and emission intensity ratio of hydrogen radicals to bromine radicals (O/Br). The electric current values of upper and lower coils of the solenoid coils 106 are varied as variable process parameters so as to change the magnetic field 105 in the vacuum chamber 104. Other process parameters are set as follows: oxygen gas flow of 4 sccm; hydrogen bromide gas flow of 24 sccm; chlorine gas low of 12 sccm, input power of microwaves of 1100 W; electric discharge pressure of 0.2 Pa; power of high frequency bias of 20 W: and temperature of wafers of 20° C.

As shown in FIG. 10, the electric current values of the upper and lower coils are varied from 24.5 A and 2.5 A, respectively (24.5 A/2.5 A: denoted by "a"), to 13 A and 12.5 A, respectively (13A/12.5 A: denoted by "k"). Hereinafter, the electric current values of the solenoid coils 105 are expressed in the same way. FIG. 10 shows results obtained by plotting each selectivity with respect to the corresponding emission intensity ratio (O/Br), varying the electric current of the solenoid coils 105 from "a" to "k". The emission intensity ratio (O/Br) is measured by using emissions at a wavelength of 777 nm (oxygen radical) and emissions at a wavelength of 780 nm (bromine radicals). The selectivity is the ratio of an etch rate of polycrystalline silicon layers to that of silicon oxide underlayer.

As shown in FIG. 10, as the emission intensity ratio (O/Br) increases, the selectivity of polycrystalline silicon to silicon oxide also increases. Accordingly, by adjusting process parameters (electric current values of the solenoid coils 105, input power of the microwaves, and the like) so as to increase the emission intensity ratio (O/Br), the plasma condition is controlled so as to provide a high selectivity of polycrystalline silicon to silicon oxide.

Next, specific examples of controlling the plasma condition in the etching process based on the measured emission intensity ratio will be described.

Figure 11A:
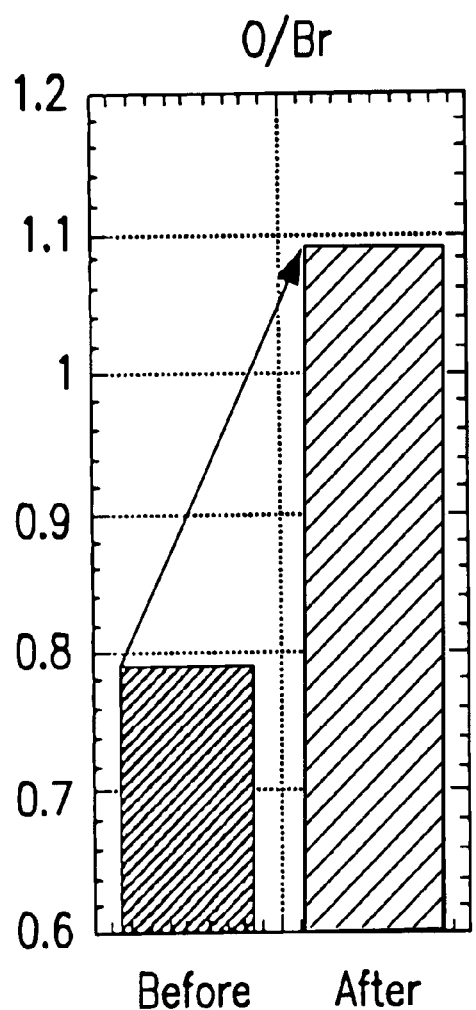
FIG. 11A is a diagram illustrating an exemplary change in the emission intensity ratio of oxygen to bromine when current values of the solenoid coils are controlled.
Figure 11B:
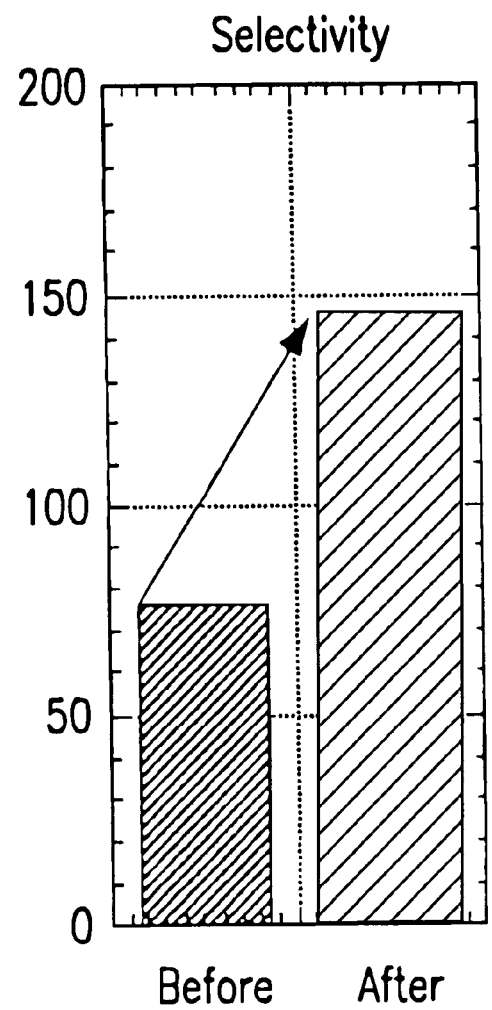
FIG. 11B is a diagram illustrating an exemplary change in the selectivity of a polycrystalline silicon layer to an oxide underlayer when current values of the solenoid coils are controlled, corresponding to FIG. 11A.

FIGS. 11A and 11B show results of an etching process in which the magnetic field is controlled by adjusting the electric current values of the upper and lower coils of the solenoid coils 105 from previous values of 15 A and 10 A, respectively, to adjusted values of 16A and 10 A, respectively, so that the emission intensity ratio (O/Br) is increased. The emission intensity ratio (O/Br) is obtained by measuring the emissions at wavelengths of 777 nm and 780 nm. In this case, the selectivity is improved significantly from 75 to 145 by this adjustment of the electric currents, as shown in FIG. 11B.

In the case where organic resist masks are used in the same adjustment, the selectivity of the polycrystalline silicon to the organic resist is improved from 1 to 3. In addition, the amount of sidewall deposits on the organic resist masks is also reduced. As a result, linewidth variations of line patterns of a high line-density (for example, linewidth:space=1:1) and isolated line patterns are both decreased, so that the size precision is improved. For example, for line patterns of linewidth 0.2 μm to 0.5 μm, the linewidth variations are reduced within about 10%.

Next, an example of adjusting the electric current values of the solenoid coils 105 so as to maximize the emission intensity ratio (O/Br) will be described. FIGS. 12A to 12C show results of an etching process in which the magnetic field is controlled by adjusting the electric current values of the solenoid coils 105 from previous values of 19 A/13.5 A (upper coil/lower coil) to adjusted values of 19 A/13 A so as to increase the emission intensity ratio (O/Br).

The selectivity of polycrystalline silicon to silicon oxide is improved as shown in FIG. 12B. The etch rate variation across the wafer is reduced from about 11.5% to about 3%, as shown in FIG. 12C. This means that the uniformity of the plasma in significantly improved. The reason is presumed to be that increasing the emission intensity ratio maximizes the plasma density by reducing absorption losses of the plasma which is energy losses in transforming the electromagnetic energy into the plasma energy and which are shown as flickers in the plasma.

Emissions from halogen radicals other than bromine radicals can also used to obtain an emission intensity ratio. For example, similar results can be obtained by measuring emissions from chlorine radicals at a wavelength of 808 nm, as well as the measurements for emissions from bromine radicals at a wavelength of 780 nm.

Controlling a plasma condition during etching can be performed, for example, as follows:

As shown in FIG. 9, the control circuit 123 can be provided with a memory unit 126 for storing respective correlations between selectivity and emission intensity ratios which are obtained from respective pairs of first and second wavelengths with respect to variable process parameters, such as shown in FIGS. 4, 6, and 10.

Process parameters such as electric current values of the solenoid coils 105, power of the microwaves, gas pressure, and the like, are detected and adjusted by the control circuit 123. The process parameters may be displayed on a monitor unit 127 which is provided to the control circuit 123, so that an operator can observe and adjust them. The control circuit 123 may includes a CPU (not shown) for monitoring and adjusting the process parameters automatically.

FIG. 21 schematically shows an example of controlling the plasma condition. The control circuit 123 determines an emission intensity ratio $\epsilon 1/\epsilon 2$ of the current plasma condition from emissions at predetermined wavelengths. Specifically, emissions at first and second wavelengths from the plasma 107 are detected in order to measure the emission intensities $\epsilon 1$ and $\epsilon 2$, respectively, via the optical system 131, the emission spectrometer 121, and the area sensor 122, as described above (step S10).

The emission intensity ratio $\epsilon 1/\epsilon 2$, which is calculated by the control circuit 123 based on the measured emission intensities $\epsilon 1$ and $\epsilon 2$, is compared with a predefined value $\epsilon 0$ (step S11). The predefined value $\epsilon 0$ is an emission intensity ratio corresponding to a required value of the selectivity in the etching. The value $\epsilon 0$ can obtained from the corresponding correlation between the selectivity and the emission intensity ratio $\epsilon 1/\epsilon 2$, which is stored in the memory unit 126.

In the case where the required selectivity is not obtained in the current plasma condition (i.e., $\epsilon 1/\epsilon 2$ is not greater than $\epsilon 0$ in step S11), one process parameter is selected from the variable process parameters for controlling the current plasma condition (step S12). The process parameter may be selected by an operator observing the monitor unit 127 or automatically selected using a CPU in the control circuit 123, which is specifically programmed to perform such selection based on the correlations associated with the memory unit 125.

The control circuit 123 adjusts the selected process parameter based on the correlation between the selectivity and the emission intensity ratio $\epsilon 1/\epsilon 2$ with respect to the selected process parameter, which is provided from the memory unit 126 (step S13). The adjustment can be performed via the corresponding one of control signals S1 to S3, for example.

Then, steps S10 and S11 are performed again. If the desired emission intensity ratio is not yet obtained, steps S12 and S13 are performed. In this case, in step S12, the same process parameter as that of the previous adjustment may be selected, or another process parameter may be selected among the variable process parameters. If in stop S11 it is determined that $\epsilon 1/\epsilon 2$ is greater than $\epsilon 0$, the adjustment operation ends. However, the same operation shown in FIG. 21 may be repeated periodically as will be appreciated.

As described above; according to the present invention, the number of variable process parameter is not limited to one, but a plurality of process parameters can be used in order to control the plasma condition.

In this example, the wavelength of 777 nm (oxygen radicals) is used as a first wavelength, and the wavelength of 780 nm or 808 nm (halogen radicals) is used as a second wavelength, in order to obtain the emission intensity ratio. Intensities of emissions having these wavelengths are close, so that the etching can be controlled by using these wavelengths more stably than by using other wavelengths. In addition, a relatively small difference between the first and second wavelengths minimizes the wavelength dependency of the measurement, which is influenced by dirt of the window 124. However, the wavelengths to be measured are not limited to these, but any wavelengths specifying oxygen radicals and halogen radicals may be used.

This example has been explained using the ECR plasma etching apparatus 130, however, the present invention is not limited to ECR plasma etching apparatuses. The present invention can be applied to other plasma etchers such as RIE apparatuses.

EXAMPLE 3

In this example, another method for controlling plasma conditions in the plasma etching apparatus 130 (shown in FIG. 9) will be described. In this example, oxygen gas plasma is generated and two emissions which have different wavelengths (first and second wavelengths) representing different excited states of oxygen is measured to obtain the emission intensity ratio. The plasma conditions are controlled using process parameters for which the emission intensity ratio is measured, in a similar manner as explained in Example 2.

In the plasma etching apparatus 130, silicon material layers formed on oxide underlayers (silicon oxide) are etched using organic resist masks in plasma of a gas mixture including halogen and/or halide gas and oxygen gas. In this example, a gas mixture including hydrogen bromide and chlorine is used as halogen/halide gas.

In this example, emissions at a wavelength of 777 nm which are emitted by transitions between excited quintet states of oxygen radicals and emissions at a wavelength of 844 nm which are emitted by transitions between excited triplet states of oxygen radicals are measured so as to obtain the emission intensity ratio. Oxygen radicals in excited quintet states are at an energy range different from those in exited triplet states. Thus, the emission intensity ratio of excited quintet states to excited triplet states (777 nm/844 nm) is presumably represents reactivity of oxygen radicals in the plasma.

Selectivity and the emission intensity ratio (777 nm/844 nm) are measured for various plasma conditions by varying process parameters in the plasma etching apparatus 130. FIG. 13 shows results of the measurements. In FIG. 13, the ordinate denotes the selectivity of polycrystalline silicon layers to oxide underlayers, and the abscissa denotes the emission intensity ratio (777 nm/844 nm) of oxygen radicals. In FIG. 13, solid circles (●) represent results obtained by varying the pressure for electric discharge, squares (■) represent results obtained by varying power of the microwaves, and triangles and diamonds (▲, ♦) represent results obtained by varying electric current values of the solenoid coils 105.

As shown in FIG. 13, the selectivity and the emission intensity ratio (777 nm/844 nm) exhibit a positive correlation. The selectivity of polycrystalline silicon layers to oxide underlayers can be increased by controlling the process parameters so as to increase the emission intensity ratio (777 nm/844 nm), with respect to each of the process parameters of pressure, current, and power.

FIG. 14 shows results of measurements of the selectivity of polycrystalline silicon layers to organic resist masks. In FIG. 14, the ordinate denotes the selectivity of polycrystalline silicon layers to organic resist masks, and the abscissa denotes the emission intensity ratio (777 nm/844 nm) of oxygen radicals. Variable process parameters are the same as those shown in FIG. 13.

As shown in FIG. 14, the selectivity and the emission intensity ratio (777 nm/844 nm) exhibit a positive correlation. The selectivity of polycrystalline silicon layers to organic resist masks can be increased by controlling the process parameters so as to increase the emission intensity ratio (777 nm/844 nm).

Figure 15:
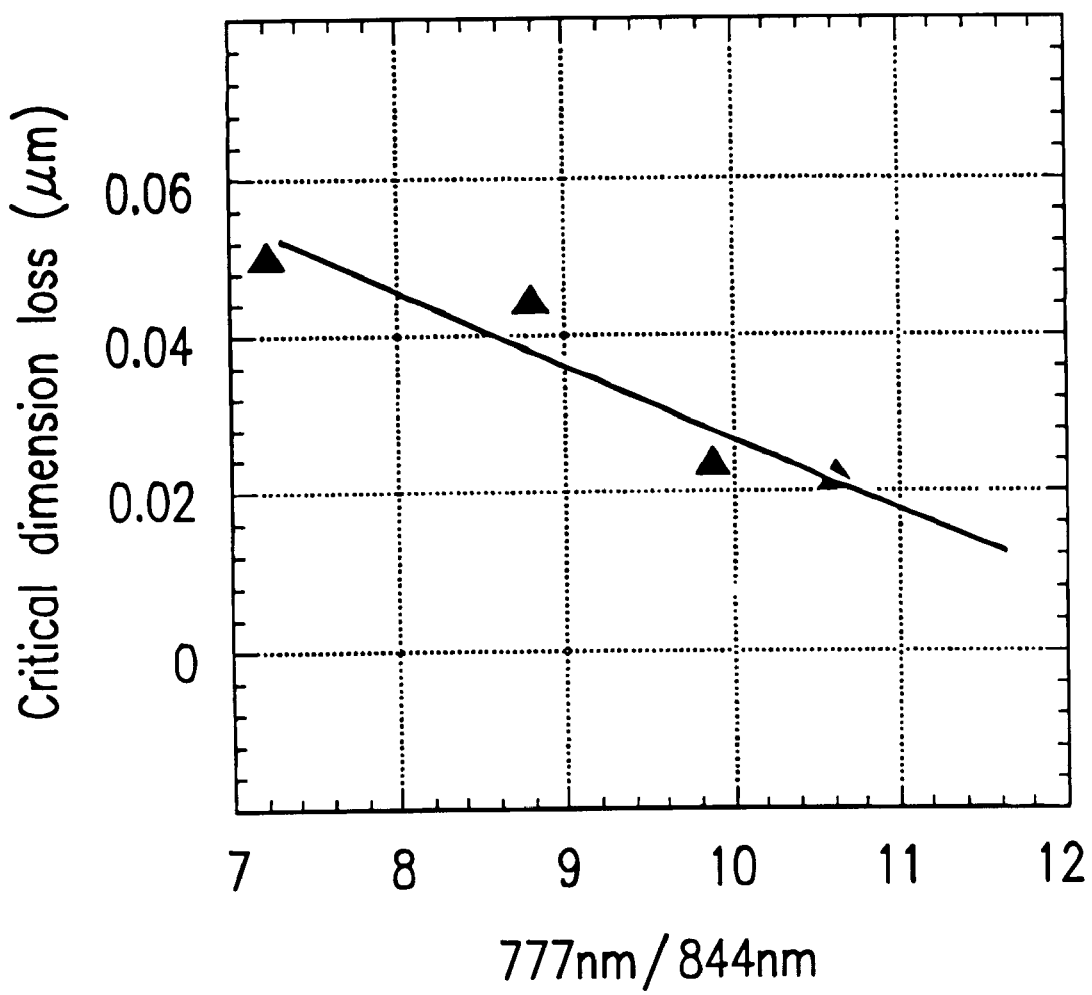
FIG. 15 is a diagram illustrating the relationship between the etch bias (critical dimension loss) and the emission intensity ratio of light having a wavelength of 777 nm to light having a wavelength of 844 nm.

Process etch biases such as linewidth variations are also reduced by controlling the process parameters so as to increase the emission intensity ratio (777 nm/844 nm). FIG. 15 shows results which are obtained by etching polycrystalline silicon layers using organic resist masks into line electrodes having a linewidth of 0.25 µm through photolithography processes. In FIG. 15, the ordinate denotes critical dimension loss as the process etch bias, and the abscissa demotes the emission intensity ratio (777 nm/844 nm). Electric current values of the solenoid coils are used as variable process parameters. As shown in FIG. 15, the process etch bias (critical dimension loss) is reduced by controlling the process parameters so as to increase the emission intensity ratio (777 nm/844 nm). This is because sidewall deposits on organic resist masks are reduced, as described above in Example 1.

As described above, by controlling the process parameters so as to increase the emission intensity ratio (777 nm/844 nm), both the selectivity of polycrystalline silicon layers to oxide underlayers and the selectivity of polycrystalline silicon layers to organic resist masks can be increased. Furthermore, the process etch bias (critical dimension lose) is also reduced and the size precision is improved by controlling the process parameters so as to increase the emission intensity ratio (777 nm/844 nm).

The emission intensity ratio (777 nm/844 nm) is increased in the cases where: gas pressure of the electric discharge of the plasma etching apparatus is increased; input power of the microwaves is increased; and electric current values of the solenoid coils are adjusted so that a position of the ECR region (875 gauss) of the magnetic field is placed close to the wafers, or so that a gradient of the magnetic field in vicinity of the ECR region is minimized.

Wavelengths of emissions to be measured are not limited to those of 777 nm and 844 nm. Since oxygen radicals have a plurality of excited quintet states and triplet stats, respectively, other wavelengths also can be used in order to obtain the emission intensity ratio. For example, emissions having a wavelength of 395 nm from oxygen radicals in excited quintet states and emissions having wavelength of 437 nm from oxygen radicals in excited triplet states can also be used to obtain the emission intensity ratio, though the wavelengths of 777 run and 844 nm provide more accurate controlling of the etching condition.

Next, another example is described, in which emissions from oxygen ions and oxygen radicals are measured. In this example, emissions having a wavelength of 588 nm which are emitted by oxygen ions and emissions having a wavelength of 844 nm which are emitted by transitions between excited triplet states of oxygen radicals are measured so as to obtain the emission intensity ratio.

Figure 16:
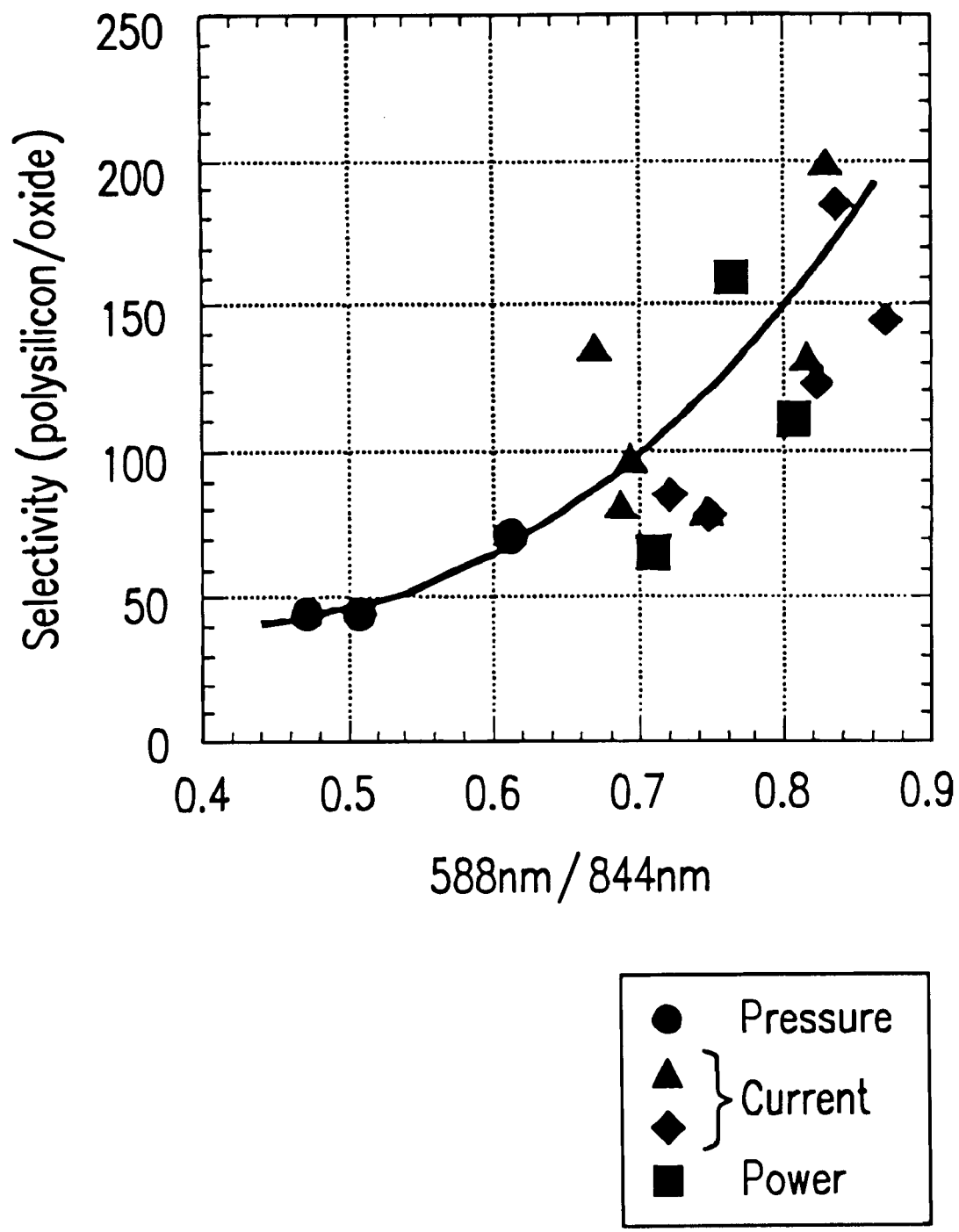
FIG. 16 is a diagram illustrating the relationship between the selectivity of polycrystalline silicon layers to oxide underlayers and the emission intensity ratio of the light having wavelength of 588 nm to the light having wavelength of 844 nm.

FIG. 16 shows results of the measurements. In FIG. 16, the ordinate denotes the selectivity of polycrystalline silicon layers to oxide underlayers, and the abscissa denotes the emission intensity ratio (588 nm/844 nm) of oxygen ions to oxygen radicals. In FIG. 16, solid circles (●) represent results obtained by varying a pressure for electric discharge, squares (■) represent results obtained by varying a power of the microwaves, and triangles and diamonds (▲, ♦) represent results obtained by varying electric current values of the solenoid coils 105.

As shown in FIG. 16, the selectivity and the emission intensity ratio (588 nm/844 nm) exhibit a positive correlation. The selectivity of polycrystalline silicon layers to oxide underlayers can be increased by controlling the process parameters so as to increase the emission intensity ratio (588 nm/844 nm), with respect to all the process parameters of pressure, current, and power.

Figure 17:
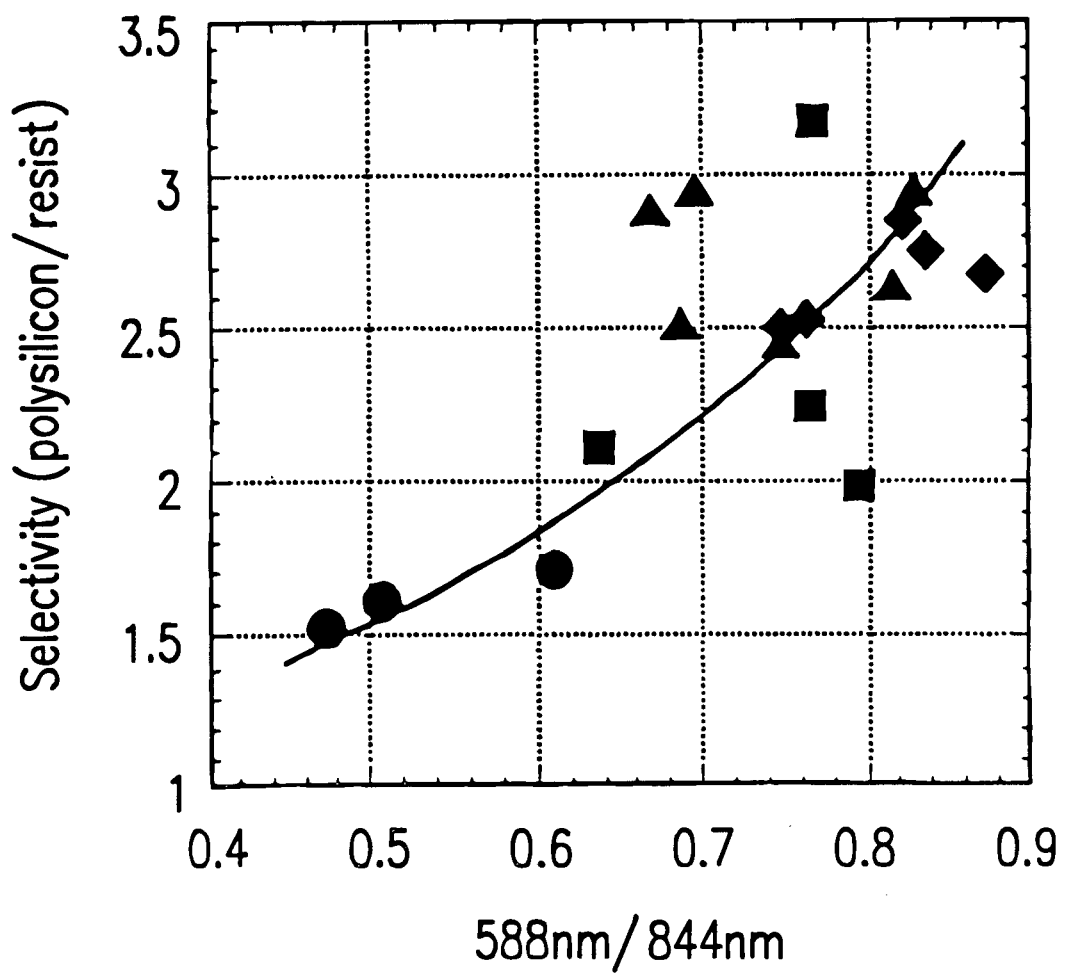
FIG. 17 is a diagram illustrating the relationship between the selectivity of polycrystalline silicon layers to resist masks and the emission intensity ratio of light having a wavelength of 588 nm to light having a wavelength of 844 nm.

FIG. 17 shows results of measurements of the selectivity of polycrystalline silicon layers to organic resist masks. In FIG. 17, the ordinate denotes the selectivity of polycrystalline silicon layers to organic resist masks, and the abscissa denotes the emission intensity ratio (588 nm/844 nm) of oxygen ions to oxygen radicals. Variable process parameters are the same as those shown in FIG. 16.

As shown in FIG. 17, the selectivity and the emission intensity ratio (588 nm/844 nm) exhibit a positive correlation. The selectivity of polycrystalline silicon layers to organic resist masks can be increased by controlling the process parameters so as to increase the emission intensity ratio (588 nm/544 nm).

Figure 18:
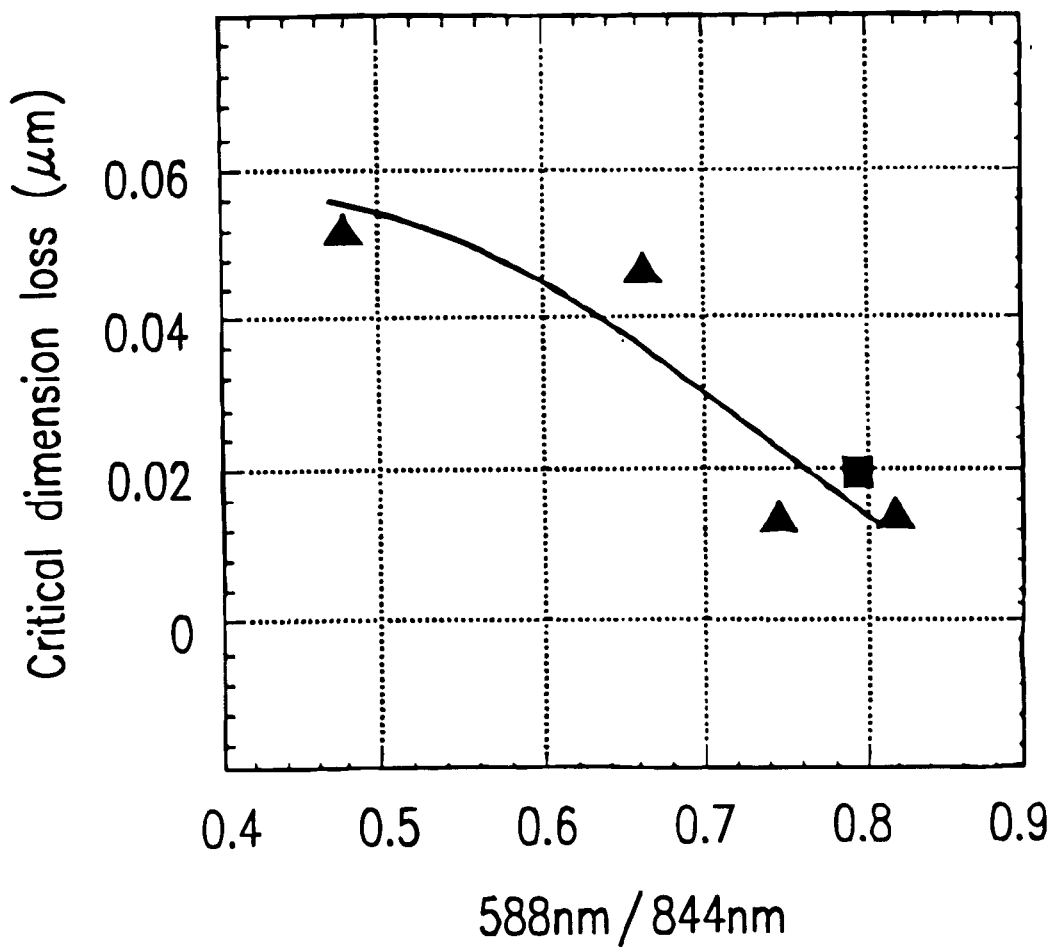
FIG. 18 is a diagram illustrating the relationship between the etch bias (critical dimension loss) and the emission intensity ratio of light having a wavelength of 588 nm to light having a wavelength of 844 nm.

Process etch biases such as linewidth variations are also reduced by controlling the process parameters so as to increase the emission intensity ratio (588 nm/844 nm). FIG. 15 shows results which are obtained by etching polycrystalline silicon layers using organic resist masks into line electrodes having a linewidth of 0.25 µm through photolithography processes. In FIG. 18 the ordinate denotes critical dimension loss as the process etch bias, and the abscissa denotes the emission intensity ratio (588 nm/844 nm). Electric current values of the solenoid coils and an input power of the microwaves are used as variable process parameters. As shown in FIG. 18, the process etch bias (critical dimension loss) is reduced by controlling the process parameters so as to increase the emission intensity ratio (588 nm/844 nm).

As described above, by controlling the process parameters so as to increase the emission intensity ratio (588 nm/844 nm), both the selectivity of polycrystalline Silicon layers to oxide underlayers and the selectivity of polycrystalline silicon layers to organic resist masks can be increased. Furthermore, the process etch bias (critical dimension loss) is also reduced so as to increase the size precision by controlling the process parameters so as to increase the emission intensity ratio (588 nm/844 nm).

Wavelengths of emissions to be measured are not limited to those of 588 nm from oxygen ions and 844 nm from oxygen radicals. For example, emissions having a wavelength of 560 nm from oxygen ions and emissions having wavelength of 437 nm from oxygen radicals in an excited triplet state can also be used to obtain the emission intensity ratio, though the wavelengths of 588 nm and 844 nm provide more accurate controlling of the etching condition.

In Example 2 and Example 3, as halogen gasses in the gas mixture, hydrogen bromide and chlorine are used. However, the present invention is not limited to this. Either one of hydrogen bromide or chlorine can be used as a single halogen gas in the gas mixture. Silicon material layers to be etched are not limited to those made of polycrystalline silicon without impurities. The present invention can be applied to the etching of silicon material layers made of polycrystalline silicon doped with impurities, monocrystalline silicon, and amorphous silicon. In addition; oxide underlayers (gate insulating films) are not limited to silicon oxide layers. Oxide underlayers may be made of silicon nitride oxide including nitrogen.

EXAMPLE 4

Next, a method for diagnosing a function of plasma etching apparatuses and a method for estimating selectivity in an actual etching process in fabrication of semiconductor devices will be described. In general, plasma is first generated by electric discharge in a vacuum chamber in a plasma etching apparatus. Prior to etching target wafers, the plasma is generated with dummy wafers placed on a wafer stage in a reaction chamber so emission intensity ratio of the plasma during the etching of the dummy wafers, as described above in Examples 1 to 3, selectivity obtained in the current plasma condition in the etching apparatus can be estimated.

In addition, operation malfunctions of the plasma etching apparatus can be detected by comparing the measured emission intensity ratio to reference emission intensity ratios which were obtained from the plasma etching apparatus operating normally. The reference emission intensity ratios may be stored in a memory unit such as the memory unit 126 provided to the control circuit 123 of the ECR plasma etching apparatus 130, as explained above in Example 2.

For example, malfunctions of the plasma etching apparatus such as a degradation in the exhaust rats of a vacuum pump, inefficiency of a magnetron generating microwaves, a poor performance of a mass-flow controller, and the like, change the electric discharge and the plasma condition. Changes in the plasma condition cause variation in the emission intensity ratio. Thus, by comparing the measured value of emission intensity ratio to the normal values thereof, the plasma etching apparatus can be diagnosed so as to detect malfunctions, if any. By measuring the emission intensity ratio without performing a specific etching process, malfunctions of the plasma etching apparatus itself can be detected avoiding influences from material of the wafers or masks.

Plasma condition is controlled by using a plurality of process parameters rather than a single process parameter. By making records for reference emission intensity ratios with respect to each of the process parameters, it can be found which process parameter is associated with the malfunction of the plasma etching apparatus using multivariate analysis.

Etching of dummy wafers does not require end point detections. Thus, the above described diagnosing method of the present invention can be performed for available plasma etching apparatuses by using an optical system and an emission spectrometer instead of an end point detection device.

The method for diagnosing the plasma etching apparatus of the present invention can also be performed for plasma etching apparatuses in which oxygen gas is not used in the etching process, as described below.

At first, before using the etching apparatus to etch target wafers, a gas mixture of oxygen gas and halogen gas, or oxygen gas and inert gas such as argon gas is introduced into a vacuum chamber so as to generate plasma by electric discharge. Emission intensity ratio is measured and compared with reference values of emission intensity ratio which are obtained from the etching apparatus operating normally. Thus, once reference values of emission intensity ratio is obtained for an etching apparatus, by measuring the emission intensity ratio using a gas mixture containing oxygen, the etching apparatus can be diagnosed to detect malfunctions thereof prior to performing the etching process.

Gas mixtures having a combination of a gas including oxygen and a halogen gas can be used for the diagnosis. For example, a gas mixture of oxygen and nitrogen, carbon dioxide and chlorine, oxygen and hydrogen bromide, or the like can be used. Gas mixtures having a combination of oxygen gas and a inert gas such as argon or helium may used for the diagnosis. A gas mixture of oxygen and argon is easer to measure the emission intensity ratio than that of oxygen and helium, since emission peaks of oxygen and helium are so close that separation of emissions is relatively difficult.

By using the plasma etching apparatus and method of the present invention described above in Examples 2 and 3, the emission intensity ratio can be measured during etching processes of target wafers. Therefore, plasma conditions and functions of the plasma etching apparatus can be monitored during etching processes, as well as estimation of selectivity and detection of malfunction prior to the etching. The plasma etching apparatus of the present invention can also serve as a detector of plasma condition and operation function, and an auto-tuner for optimizing the plasma condition so as to, for example, realize a high selectivity.

EXAMPLE 5

First, basic principles of the fifth example of the present invention will be described. In this example, a plasma etching apparatus and method for etching silicon material layers formed on oxide underlayers of silicon oxide using an etchant gas mixture including halogen and/or halide (halogen/halide) gas and oxygen gas is described.

In this example, relative density of oxygen radicals to halogen radicals is increased without the changing flow rate of a process gas (gas mixture) or ratio of component gases of the process gas. The applicants have found that selectivity of silicon material layers to oxide underlayers is improved by increasing the relative density of oxygen radicals to halogen radicals in the plasma, not by increasing flow rate of oxygen gas. More specifically, the relative density of oxygen radicals is significantly increased in high density plasma having density more then $10^{10}/cm^3$. The reason why is presumed that high density plasma is required to enhance dissociation and excitation of oxygen gas which has a high dissociation energy, while halogen and halide gases having a relatively low dissociation energy are well dissociated and excited in a relatively low density plasma of a density about $10^9/cm^3$.

Furthermore, the applicants have found that not only the selectivity of silicon material layers to oxide underlayers but also the selectivity of silicon material layers to organic resist masks is improved by using the plasma having a high relative density of oxygen radicals to halogen radicals. In addition, it has been found that banking deposits on sidewalls of the organic resist masks due to by-products of etching reactions are also reduced by increasing the relative density of oxygen radicals.

In this example, oxygen gas is introduced into a vacuum chamber of the plasma etching apparatus though a different gas inlet from that for halogen/halide gas. The oxygen gas is introduced into a first region of a magnetic field having a higher intensity in the vacuum chamber, in which plasma having a high density or a high electron energy is generated. The oxygen gas is effectively dissociated and excited in the first region of the magnetic field.

On the other hand, halogen/halide gas is introduced via another gas inlet into a second region of the magnetic field having a lower intensity in the vacuum chamber close to wafers in a reaction camber. The halogen/halide gas is dissociated and excited in the second region of the magnetic field by free electrons in the plasma which is transported from the first region. During transportation, plasma density is lowered by recombination reactions and the like. The halogen/halide gas is sufficiently dissociated and excited in the plasma of a relatively low density ($10^9/cm^3$ to $10^{10}/cm^3$), since the dissociation energy of halogen/halide gas is smaller than that of oxygen gas. Thus, the etch rate is not decreased by introducing the halogen/halide gas into the second region of a weaker magnetic field.

The relative density of oxygen radicals to halogen radicals is increased by introducing oxygen gas and halogen/halide gas in different regions of the magnetic field as described above. An increase in the relative density of oxygen improves the selectivity of silicon material layers to oxide underlayers with organic resist masks. In addition, plasma density in the vicinity of wafers is lowered, and insulation breakdown of oxide underlayers due to electron build-up in the substrate surfaces is prevented so as to decrease damage to oxide underlayers.

Figure 19:
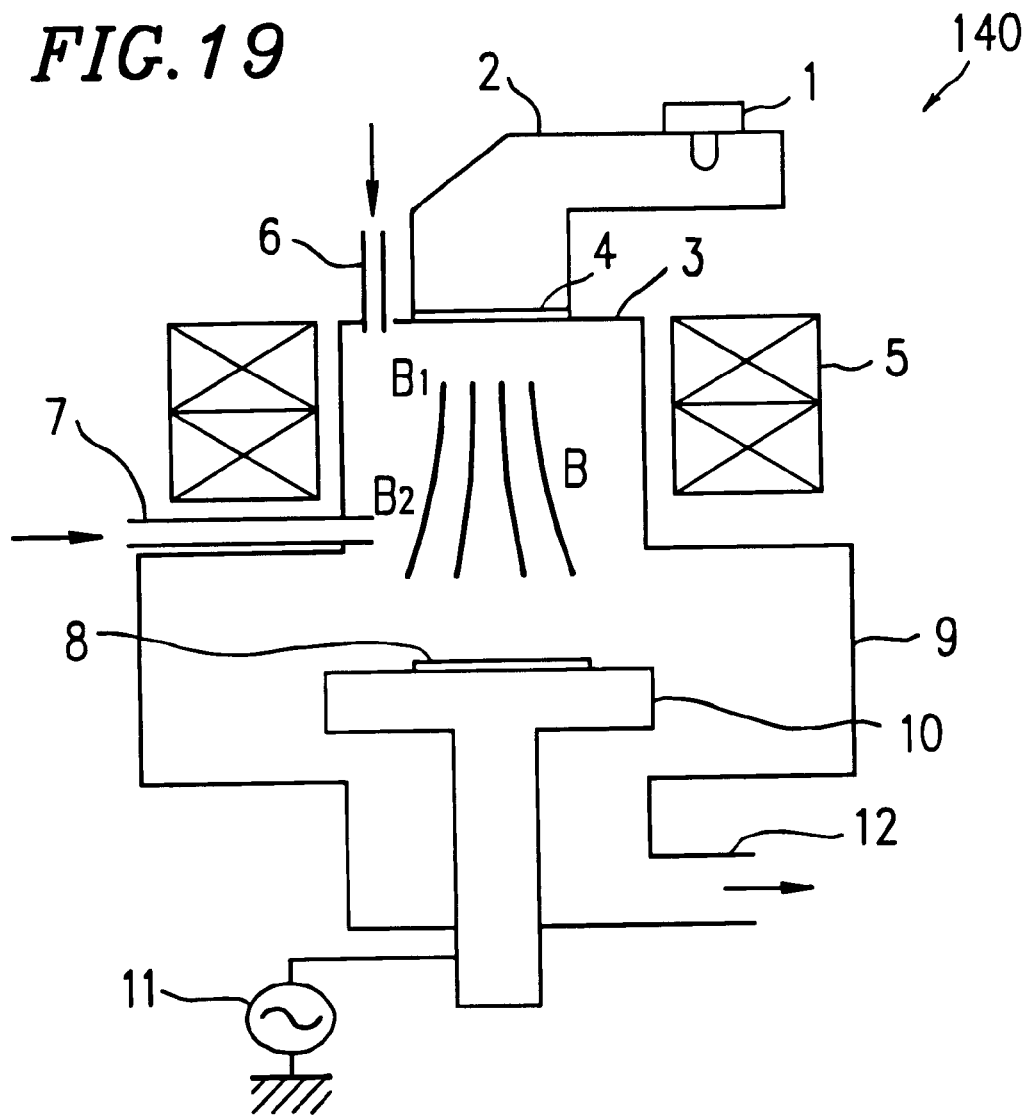
FIG. 19 is a partial schematic view of an ECR plasma etching apparatus of another example according to the present invention.

A specific example is now described below. FIG. 19 schematically shows a cross-sectional view of an ECR plasma etching apparatus 140 of this example according to the present invention. Units of the ECR plasma etching apparatus 140 corresponding to those of the ECR plasma etching apparatus 110 described in Example 1 are denoted by the same numerical numbers. Although not shown in FIG. 19, the ECR plasma etching apparatus 140 includes a control system for controlling plasma conditions via process parameters, such as that of the ECR plasma etching apparatus 130 shown in FIG. 9. The relative density of oxygen radicals to halogen radicals can be estimated, for example, by measuring an emission intensity ratio of the oxygen radicals to halogen radicals in the same manner as discussed above in Examples 1–3.

As shown in FIG. 19, the ECR plasma etching apparatus 140 includes a magnetron 1 for generating microwaves at 2.45 GHz, a waveguide 2 for introducing the microwaves into a vacuum chamber 3 in which the plasma is generated, solenoid coils 5 provided around the vacuum chamber 3 for generating a magnetic field B in the vacuum chamber 3, and a reaction camber 9 in which etching processes are performed. The microwaves generated by the magnetron 1 are guided by the waveguide 2 into the vacuum chamber 3 through a window 4 made of material such as silica glass which transmits the microwaves. The vacuum chamber 3 comprises a first gas inlet 6 and a second gas inlet 7 opening at respective positions of the vacuum chamber 3.

As shown in FIG. 19, the magnetic field B is strong in vicinity of the window 4, so that intensity of a first region $B_1$ of the magnetic field close to the window 4 has an intensity higher than that of ECR (875 G). The magnetic field B weakens along a traveling path of the microwaves, passing through the ECR intensity in a resonance region $B_r$ (not shown), to a low intensity in a second region $B_2$ in the vicinity of the reaction chamber 9. The resonance region $B_r$ is formed at an upper side of the second gas inlet 7 along a stream of the plasma transportation.

As shown in FIG. 19, the first gas inlet 6 is placed so as to introduce a first gas into the first region $B_1$ of the magnetic field in the vacuum chamber 3, while the second gas inlet 7 is placed so as to introduce a second gas into the second region $B_2$ of the magnetic field. Thus, the first gas, which is introduced into the region a, via the first gas inlet 6, is dissociated and excited by the strong magnetic field in the region $B_1$ and then in the resonance region $B_r$, so as to form high density plasma. The plasma is transported along the magnetic flux toward the reaction chamber 9 to the weaker magnetic field in the region $B_2$. The second gas, which is introduced into the region $B_2$ via the second gas inlet 7, is dissociated and excited by free electrons in the transported plasma having a lower density.

A wafer platen electrode (wafer stage) 10 for loading a wafer 8 to be etched is provided in the reaction chamber 9. The wafer platen electrode 10 is connected to a high frequency power supply 11 and is supplied with a high frequency bias voltage. The reaction chamber 9 is provided with a gas exhaust 12 to which a vacuum exhaust system (not shown) such as a turbo molecular pump having a large exhaust rate is coupled. Turbo molecular pumps are vacuum pumps which exhaust gas molecules mechanically by a turbo fin rotating at a high speed. Turbo molecular pumps are suitable for fast exhaust and used to obtain middle to high vacuum of $10^{-2}$ to $10^{-5}$ Pa.

Next, an etching method using the ECR plasma etching apparatus 140 will be described. In this example, polycrystalline silicon material layers without impurities are patterned into gate electrodes by etching. A gas mixture of hydrogen bromide and chlorine (the second gas described above) and oxygen gas (the first gas described above) are used as process gases.

Figure 20A:
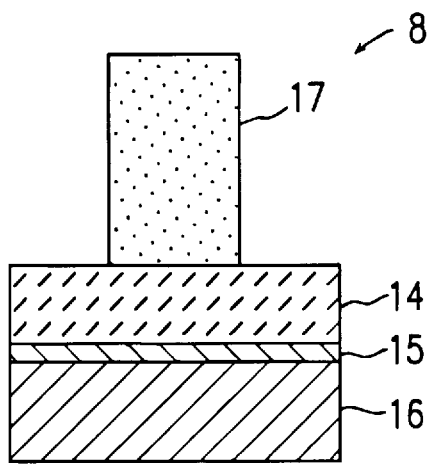
FIGS. 20A to 20C are diagrams illustrating the steps of polycrystalline silicon etching using the dry etching apparatus and method of the present invention.

As shown in FIG. 20A, the wafer 8 includes a silicon substrate 16, a gate insulation film (oxide underlayer of silicon oxide) 15 formed on the silicon substrate 16, a polycrystalline silicon layer 14 formed on the gate insulation film 15, which is not doped with impurities, and an organic resist mask 17 having a predetermined pattern formed on the polycrystalline silicon layer 14.

As shown in FIG. 19, oxygen gas (4 sccm) is introduced into the vacuum chamber 3 via the first gas inlet 6. The plasma is generated under the conditions of a microwave input power of 1100 W and a gas pressure of 0.2 Pa. At the same time, a gas mixture of hydrogen bromide (24 sccm) and chlorine (12 sccm) is introduce into the vacuum chamber 3 in a region close to the reaction chamber 9 via the second gas inlet 7. The wafer 8 is etched under the conditions in which a power of the high-frequency bias of 20 W is applied to the wafer platen electrode 10, and a wafer temperature is 20° C.

Selectivity obtained in the above conditions of process parameters is as high as follows: the selectivity of the polycrystalline silicon layer 14 to the oxide underlayer 15 is about 200; and the selectivity of the polycrystalline silicon layer 14 to the organic resist mask 17 is about 3.

Figure 20B:
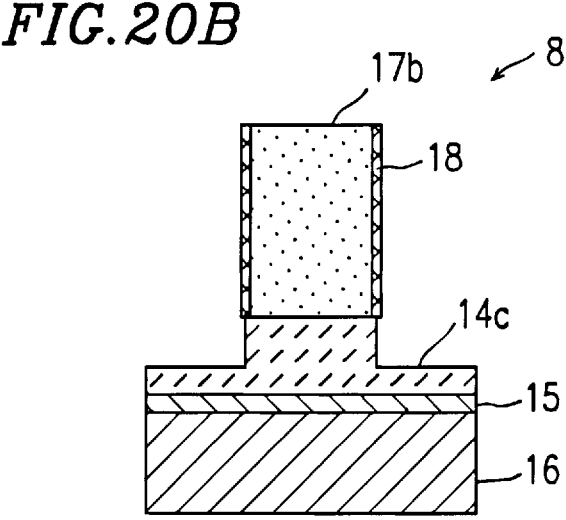
Figure 20C:
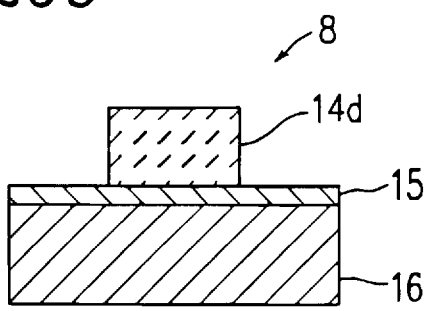

As show in FIG. 20B, banking deposits 18, which are by-products of silicon oxide produced in the etching reactions, are formed on sidewalls of organic resist mask 17b during the etching process. Nevertheless, the banking deposits 18 is sufficiently thin so that they do not affect the mask pattern of the organic resist musk 17b. As shown in FIG. 20C, the processed polycrystalline silicon layer 14d has a pattern substantially in accordance with the original mask pattern of the organic resist mask 17. For example, in, the case of line patterns of linewidth 0.2 $\mu$m to 0.5 $\mu$m, the linewidth variations of the processed polycrystalline silicon layer 14d are reduced within about 10%, with respect to both of high line-density (for example, linewidth:space=1:1) patterns and isolated line patterns.

In this example, oxygen gas is used as the first as introduced via the first gas inlet 6. The first gas is not limited to pure oxygen gas, but a gas mixture of oxygen gas and an inert gas such as helium may be used. In this case, stability of the electric discharge in the vacuum chamber 3 and uniformity of the plasma can be further improved.

In this example, a gas mixture of hydrogen bromide and chlorine is used as the second gas (halogen/halide gas) introduced via the second gas inlet 7. The halogen/halide gas is not limited to a gas mixture, but a pure hydrogen bromide gas or pure chlorine gas may be used for an etchant gas. By using a halogen/halide gas which includes at least one of bromine-based gas and chlorine-based gas, anisotropy of the etching can be improved so as to increase the selectivity of silicon material layers to oxide underlayers.

In order to increase the selectivity so as to reduce the process etch variation, it is preferable to realize a higher relative density of oxygen radicals to halogen radicals in the reaction chamber 9. The plasma having a high density in the resonance region $B_r$ of the magnetic field increases the relative density of oxygen radicals. Thus, process parameters are controlled so as to increase the plasma density in the resonance region $B_r$, for example, by increasing an input power of the microwaves from 900 W to 1200 W, and/or by reducing a gas pressure to 0.3 Pa to 0.07 Pa.

In order to realize a higher relative density of oxygen radicals to halogen radicals, the resonance region $B_r$ of the magnetic field is preferably placed so that a distance (height) from the wafer 8 is minimized, as far as the electric discharge is stable. For example, a preferable value of the distance (the height from the wafer 8) is in a range of 120 mm to 150 mm, obtained by varying the height from 110 mm to 200 mm, which generates the high density plasma effectively.

A gradient of the magnetic field intensity in the resonance region Br is preferably minimized, as far as the electric discharge is stable. For example, a preferable value of the gradient of the magnetic field intensity is in a range of 30 G/cm to 55 G/cm, obtained by varying the intensity gradient from 30 G/cm to 70 G/cm, which generates the high density plasma effectively.

In this example, etching of polycrystalline silicon layers without impurity has been described. However, silicon material is not limited to this. Other silicon materials such as polycrystalline silicon including impurity, monocrystalline silicon, amorphous silicon, and the like can be used. The material of the gate insulation film 15 is not limited to silicon oxide, but silicon nitride oxide can also be used.

The present invention is not limited to ECR plasma etching apparatuses, but can be implemented by using other plasma apparatuses, or by combining two or more plasma apparatuses. For example, the plasma etching apparatus of the present invention may includes first and second plasma apparatus as parts thereof. The first plasma apparatus is used for generating high density plasma such as ECR plasma or helicon plasma from a first gas including oxygen gas. The high density plasma (including oxygen radicals) is transported to the second plasma apparatus in which a second gas of halogen/halide is introduced and etching processes are preformed. By using a helicon plasma apparatus as the first plasma apparatus, very high density plasma of about $10^{12}$/cm$^3$ can be generated at a relatively low pressure of about $10^{-1}$ to $10^{-2}$ Pa.

In addition, the method and apparatus of the present invention is not limited to being used for etching gate electrodes, but can be applicable to any selective etching of silicon material layers formed on oxide underlayers made of materials such as silicon oxide Or silicon nitride oxide. Thus, the present invention can be used for various fabrication processes of semiconductor devices.

As described above, according to the present invention, by measuring emissions from the plasma having two different wavelengths so as to obtain the emission intensity ratio thereof, the plasma condition is controlled based on the emission intensity ratio which is associated with selectivity. By adjusting process parameters of the plasma etching apparatus so as to increase the emission intensity ratio, the plasma condition can be optimized in which the selectivity of silicon material layers to oxide underlayers and the selectivity of silicon material layers to organic resist masks are both improved; sufficient size precision in realized by reducing amount of banking deposits on sidewalls of the organic resist masks during the etching; and uniformity of the etch rate over a surface of the wafer.

By using the emission intensity ratio rather than the emission intensity itself, accurate control of the plasma condition is realized since the emission intensity ratio it sufficiently free from influences of shape of the plasma, detecting position of the plasma and distance from an optical system for detecting emissions, dirt of the window through which emissions are detected, and the like. Therefore, reliable plasma etching can be performed by controlling the plasma based on the emission intensity ratio.

In addition, the emission intensity ratio can be measured without disturbing the plasma using an optical system which has a relatively small size. This makes it possible to implement the plasma etching apparatus realizing an accurate control of plasma condition and reliable etching, without increasing size and cost of the plasma etching apparatus.

According to the present invention, by increasing efficiency of producing oxygen radicals, relative density of the oxygen radicals in the plasma is increased without increasing a flow rate of oxygen gas, leaving the plasma density in vicinity of the wafers relatively low. This makes it possible to improve the selectivity of silicon material layers to oxide underlayers and to reduce the damage of oxide underlayers. Thus, oxide underlayers can be formed thinner without seriously damaging underlying substrates. Furthermore, the selectivity of silicon material layers to organic resist masks is also improved and amount of banking deposits of reaction bi-products on sidewalls of the organic resist masks are reduced. This reduces size variations so as to realize a sufficiently high size precision required for the microminiaturization of semiconductor devices.

The relatively lower plasma density in the vicinity of the wafers prevents insulation breakdown of oxide underlayers due to electron build-up in substrate surfaces and local anomaly of the etching such as notches of silicon material layers, reducing damages by the etching process and degradation of oxide underlayers.

According to the present invention, etching-produced deposits produced by recombination of by-products of etching reactions and etching-produced silicon oxide produced by dissociation of by-products of silicon material etching are prevented from being formed on substrate surfaces and sidewalls of organic resist masks. This makes it easy to control etch rates.

According to the present invention, drawbacks caused by organic resist masks used in the conventional etching methods and apparatuses are eliminated, so that organic resist masks are advantageously utilized so as to improve size precision in the etching process and reduce the number of steps required for the fabrication of semiconductor devices.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for diagnosing a function of a plasma etching apparatus including the steps of:

generating plasma of a gas mixture including halogen and oxygen in a predetermined condition;

measuring an intensity of one of first emissions from the plasma at a first wavelength and an intensity of one of second emissions from the plasma at a second wavelength;

obtaining a ratio of the intensity of the one of first emissions to that of the one of second emissions;

comparing the obtained emission intensity ratio with an emission intensity ratio which is previously measured for a plasma condition when the plasma etching apparatus operates normally.

2. A method for diagnosing a function of a plasma etching apparatus according to claim 1, wherein in the step of measuring the intensities, emissions from oxygen radicals and emissions from halogen radicals are measured as the first and second emissions, respectively.

3. A method for diagnosing a function of a plasma etching apparatus according to claim 2, wherein in the step of measuring intensities, emissions from oxygen radicals at a wavelength of 777 nm and emissions from bromine radicals at a wavelength of 780 nm are measured.

4. A method for diagnosing a function of a plasma etching apparatus according to claim 2, wherein in the step of measuring intensities, emissions from oxygen radicals at a wavelength of 777 nm and emissions from chlorine radicals at a wavelength of 808 nm are measured.

5. A method for diagnosing a function of a plasma etching apparatus according to claim 1, wherein the gas mixture includes at least one of bromine and chlorine as the halogen.

6. A method for diagnosing a function of a plasma etching apparatus according to claim 1, wherein previous measuring of the emission intensity ratio is performed with respect to process parameters for controlling the plasma condition, and wherein the comparing step includes analyzing the obtained and previously measured emission intensity ratios with respect to the process parameters.

* * * * *